United States Patent
Kim et al.

(10) Patent No.: US 6,172,260 B1
(45) Date of Patent: Jan. 9, 2001

(54) PREPARATION OF HIGH DYE-YIELD COUPLERS AND INTERMEDIATES USEFUL THEREIN

(75) Inventors: Chang-Kyu Kim, Pittsford; Jared B. Mooberry; David Hoke, both of Rochester; James J. Seifert, Hilton, all of NY (US)

(73) Assignee: Eastman Kodak Company, Rochester, NY (US)

(*) Notice: Under 35 U.S.C. 154(b), the term of this patent shall be extended for 0 days.

(21) Appl. No.: 09/224,476

(22) Filed: Dec. 31, 1998

(51) Int. Cl.$^7$ .................................................. C07C 271/04
(52) U.S. Cl. ........................ 562/844; 562/846; 548/196
(58) Field of Search ...................... 562/844, 846; 548/196

(56) References Cited

U.S. PATENT DOCUMENTS

| | | | |
|---|---|---|---|
| 4,840,884 | 6/1989 | Mooberry et al. | 430/557 |
| 5,447,819 | 9/1995 | Mooberry et al. | 430/226 |
| 5,457,004 | 10/1995 | Mooberry et al. | 430/226 |

FOREIGN PATENT DOCUMENTS

| | | |
|---|---|---|
| 247 848 | 12/1987 | (EP) . |
| 950 922 | 10/1999 | (EP) . |
| 2261005 * | 2/1975 | (FR) . |
| 98/24791 | 6/1998 | (WO) . |
| 98/50030 | 11/1998 | (WO) . |

OTHER PUBLICATIONS

Ito et al., Chemical Abstracts, vol. 131, abstract 305094, 1999.*
Zheng et al., Chemical Abstracts, vol. 128, abstract 167449, 1998.*
Krantz et al., Chemical Abstracts, vol. 109, abstract 170447, 1988.*
Gadient et al., Chemical Abstracts, vol. 84, abstract 59032. 1976.*
Smith et al., Chemical Abstracts, vol. 86, abstract 190410, 1977*
L. Baiocchi, G. Corsi, G. Palazzo: "Ricerche nel campo degli indazoli.—Nota 1. Sulla ciclizzazione termica di azidi di acidi N–aril–N–benzil–carbamici", Annali Di Chimica, vol. 55, 1965, pp. 116–125.

* cited by examiner

*Primary Examiner*—Richard L. Raymond
(74) *Attorney, Agent, or Firm*—Arthur E. Kluegel

(57) ABSTRACT

Disclosed is a carbamyl chloride of an aminoarylcarbonyl compound having the structural formula I:

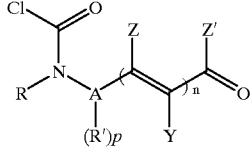

Formula I wherein
R is an alkyl, alkenyl, or aryl group;
A is an aryl (including heteroaryl) ring group;
each R' is independently an alkyl group which may form a ring with Z or Z';
p is 0, 1, 2, or 3;
each Z, Z', and Y is independently hydrogen or a substituent; and
n is 0, 1, or 2.

16 Claims, No Drawings

PREPARATION OF HIGH DYE-YIELD COUPLERS AND INTERMEDIATES USEFUL THEREIN

FIELD OF THE INVENTION

This invention relates to carbamyl chlorides of aninoarylcarbonyl compounds useful as intermediates for the preparation of photographic high dye-yield couplers, and to methods of making and using the intermediates to prepare photographic couplers.

BACKGROUND OF THE INVENTION

It has been known in the art to employ a releasable dye as the coupling-off group to provide a so-called 'high dye-yield' coupler. Such a coupler reacts with oxidized color developer to form one dye and in doing so releases a second dye. The net results are formation of two dyes with two equivalents of silver. It enables the reduction of the amount of coupler, silver, and other materials in the film layers. It also enables thinner layers which in turn reduces the amount of light scatter to improve sharpness in underlying layers. Thinner layers can also reduce the level of unwanted absorption, which can further enhance the image quality in underlying layers. The benefits of the high dye-yield couplers are thus particularly advantageous if they are placed in the uppermost layers, i.e., the blue sensitive layers, of multilayer films.

Useful high dye-yield couplers have been disclosed by J. Mooberry and S. Singer in U.S. Pat. No. 4,840,884. Mooberry, et al. have later disclosed improved high dye-yield couplers with methine dye chromophores in U.S. Pat. No. 5,457,004. The latter patent teaches the advantages of using methine dyes. Compared to couplers releasing analogous azo dyes, the couplers releasing methine dyes provide much higher extinction and superior photographic properties such as hue, Dmax, and low unwanted absorption by the coupler.

One of the obstacles in manufacturing high dye-yield couplers is difficulty of synthesis. These couplers require a fair number of synthetic steps, some of which proceed only in modest yield and are difficult to adapt to large-scale manufacture. The synthesis outlined in U.S. Pat. No. 5,457,004, for instance, involves a hooking up reaction between a hydroxy group in the coupler-timing group piece and the methine dye carbamyl chloride. The hooking up reaction proceeds in reasonable yield in case (a) where a timing group $(T)_m$ is present and the alkyl group on the nitrogen atom of the dye molecule is straight chain alkyl. When the N-alkyl group of the requisite dye carbamyl [chromophol-N(—R)—C(=O)—Cl] is branched or bulky, the reaction with the hydroxy group in coupler-timing group component is sluggish and yields of desired product are poor due to undesired side reactions. Fairly strong organic bases must be used to effect the attachment of coupler and dye components, but the desired product and starting components are easily destroyed by the base if the desired reaction is not rapid. In the case (b) where the timing group is absent (m=0), the methine dye is attached directly to the coupling site via the linking group (usually acyloxy). This requires the coupler synthesis unit to be COUP-OH (hydroxyl group attached at the coupling site) in order to react with the methine dye carbamyl chloride. Hydroxy couplers also react with the methine dye carbamyl chloride to give the desired HDY coupler in reasonable yield only when the R group is small, i.e., methyl. As the R group becomes larger and steric demands are greater, the reaction proceeds progressively poorer or not at all. In the comparative example herein (Example 2) where R=ethyl, this reaction proceeds in a modest 31% yield. Generally, as the R group increases in size the desired reaction slows down because of steric effects, but undesired reactions such as aerial oxidation of COUP-OH and reactions which decompose the dye chromophore do not necessarily decrease in rate. A competing reaction corresponding to addition of COUP-OH to the carbon-carbon double bond of the methine dye chromophore to yield dihydrofurans is particularly troublesome and prevails in the case where R is larger than ethyl, particularly in cases where R is branched alkyl. It is desirable to be able to make the desired coupler without incurring a large degree of undesired side reactions.

Preparation of straight chain alkyl aminoaryl aldeh',des is described in U.S. Pat. Nos. 5,447,819 and 5,457,004. Other methods are available. However, carbamyl chlorides of aminoarylcarbonyl compounds are not known in the literature.

It is therefore a problem to be solved to provide carbamyl chlorides of aminoarylcarbonyl compounds, a method of making them, and a method of using them in the preparation of high dye-yield couplers.

SUMMARY OF THE INVENTION

In one aspect the invention relates to a carbamyl chloride of an aminoarylcarbonyl compound having the structural Formula I:

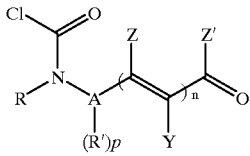

Formula I wherein:
R is an alkyl, alkenyl, or aryl group;
A is an aryl (including heteroaryl) ring group;
each R' is independently an alkyl group which may form a ring with Z or Z';
p is 0, 1, 2, or 3;
each Z, Z', and Y is independently hydrogen or a substituent; and
n is 0, 1, or 2.

In another aspect the invention provides a method of making the intermediates of Formula I, comprising the steps of:

(a) blocking the carbonyl function of an aminoarylcarbonyl compound via Schiff base formation with a hindered alkyl amine;

(b) making a carbamyl chloride of the blocked aminoarylcarbonyl compound by phosgenation; and (c) deblocking the carbamyl chloride of the blocked aminoarylcarbonyl via acid hydrolysis to regenerate the carbonyl function and give the desired carbamyl chloride of an aminoarylcarbonyl compound having formula I.

In yet another aspect the invention provides a method of using the intermediates of Formula I in the preparation of high dye-yield couplers.

The compound and methods of the invention allow the preparation of the high dye-yield couplers in much higher yields than heretofore possible.

DETAILED DESCRIPTION OF THE INVENTION

In one aspect this invention relates to intermediates useful for the preparation of high dye-yield couplers having the structural Formula I as described in the Summary of the Invention. In another aspect, this invention relates to a process for using the intermediates of Formula I in the preparation of high dye yield couplers, to make a coupler of Formula II:

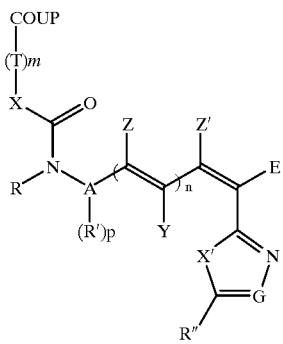

Formula II the method comprising the steps of:
(a) reacting the carbamyl chloride compound of Formula I with a coupler piece of Formula III

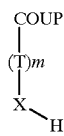

Formula III to form a carbamate link between the coupler piece and the aminoaiylcarbonyl compound,
wherein
COUP is a photographic coupler residue bonded at the coupling position to T or X and capable of coupling with oxidized color developer to form a first dye;
T is a timing group;
m is an integer from 0 to 2; and
X is O, S, or $N(R_{12})$ where $R_1$ is hydrogen or alkyl; and
(b) conducting a condensation reaction between the carbon31 portion of the coupler-timing group-aminoarylcarbonyl product of part (a) with a portion of methine dye of Formula IV as below having an active methylene group:

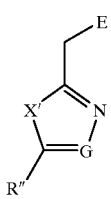

Formula IV wherein
E is an electron withdrawing group;
X' is O, S, or $N(R_2)$ where $R_2$ is hydrogen or alkyl;
G is N or $C(R_3)$ where $R_3$ is hydrogen or a substituent; and R" is a substituent linked to the heterocycle by a carbon or nitrogen atom of the substituent, provided that R" and $R_3$ may be linked to form a ring to give a high dye-yield coupler having Formula II:

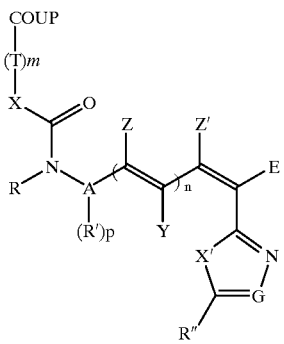

Formula II

Examples of useful COUP groups are:

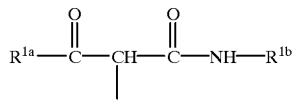

1A

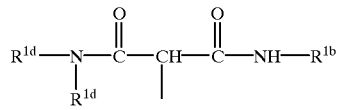

1B

A free bond from the coupling site in the above formulae indicates a position to which the coupling release group or coupling-off group is linked. In the above formulae, when $R^{1a}$ or $R^{1b}$ contains a ballast or antidiffusing group, it is selected so that the total number of carbon atoms is from 8 to 32 and preferably from 10 to 22.

$R^{1a}$ represents an aliphatic- or alicyclic-hydrocarbon group, an aryl group, an alkoxyl group, or a heterocyclic group, and each $R^{1b}$ independently represents an aryl group or a heterocyclic group.

The aliphatic- or alicyclic hydrocarbon group represented by $R^{1a}$ preferably has at most 22 carbon atoms, may be substituted or unsubstituted, and aliphatic hydrocarbon may be straight or branched. Preferred examples of the substituent for these groups represented by $R^{1a}$ are an alkoxy group, an aryloxy group, an amino group, an acylamino group, and a halogen atom. These substituents may be further substituted with at least one of these substituents repeatedly. Useful examples of the groups as $R^{1a}$ include an isopropyl group, an isobutyl group, a tert-butyl group, an isoamyl group, a tert-amyl group, a 1,1-dimethyl-butyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an cc-aminoisopropyl group, an α-(diethylamino)isopropyl group, an α-(succinimido) isopropyl group, an α-(phthalimido)isopropyl group, an α-(benzenesulfonamido)isopropyl group, and the like.

When $R^{1a}$ or $R^{1b}$ is an aryl group (especially a phenyl group), the aryl group may be substituted. The aryl group (e.g., a phenyl group) may be substituted with groups having not more than 32 carbon atoms such as an alkyl group, an alkenyl group, an alkoxy group, an alkoxycarbonyl group, an alkoxycarbonylamino group, an aliphatic- or alicyclic-amido group, an alkylsulfamoyl group, an alkylsulfonamido group, an alkylureido group, an aralkyl group and an alkyl-substituted succinimido group. This phenyl group in the aralkyl group may be further substituted with groups such as an aryloxy group, an aryloxycarbonyl group, an arylcarbamoyl group, an arylamido group, an arylsulfamoyl group, an arylsulfonamido group, and an arylureido group.

The phenyl group represented by $R^{1a}$ or $R^{1b}$ may be substituted with an amino group which may be further substituted with a lower alkyl group having from 1 to 6 carbon atoms, a hydroxyl group, —COOM and —SO$_2$M (M=H, an alkali metal atom, NH$_4$), a nitro group, a cyano group, a thiocyano group, or a halogen atom.

$R^{1a}$ or $R^{1b}$ may represent substituents resulting from condensation of a phenyl group with other rings, such as a naphthyl group, a quinolyl group, an isoquinolyl group, a chromanyl group, a coumaranyl group, and a tetrahydronaphthyl group. These substituents may be further substituted repeatedly with at least one of above-described substituents for the phenyl group represented by $R^{1a}$ or $R^{1b}$.

When $R^{1a}$ represents an alkoxy group, the alkyl moiety of the alkoxyl group can be a straight or branched alkyl group, an alkenyl group, a cycloalkyl group, or a cycloalkenyl group each having at most 32 carbon atoms, preferably at most 22 carbon atoms. These substituents may be substituted with groups such as halogen atom, an aryl group and an alkoxyl group to form a group having at most 32 carbon atoms.

When $R^{1a}$ or $R^{1b}$ represents a heterocyclic ring, the heterocyclic group is linked to a carbon atom of the carbonyl group of the acyl group in α-acylacetamido or to a nitrogen atom of the amido group through one of the carbon atoms constituting the ring. Examples of such heterocyclic rings are thiophene, furan, pyran, pyrrole, pyrazole, pyridine, pyrazine, pyrimidine, pyridazine, indolizine, imidazole, thiazole, oxazole, triazine, thiadiazine and oxazine. These groups may further have a substituent or substituents in the ring thereof. Examples of the substituents include those defined for the aryl group represented by $R^{1a}$ and $R^{1b}$.

COUP of the invention is the parent portion of the coupler. This is the portion of the coupler that combines with oxidized color developer in a conventional process to form a colored image dye. The various types of couplers are described more fully hereinafter. Typical COUP groups form yellow dyes (e.g. acylacetanilides), magenta dyes (e.g. pyrazolones or pyrazoloazoles;, or cyan dyes (e.g. phenols, naphthols or pyrazoloazoles). In the preferred embodiment of the invention the COUP group is one which forms a yellow dye such as an acylacetanilide. Suitable examples include pivaloylacetanilides, methylcyclopropylacetanilides, indoloylacetanilides, and benzoylac etanilides.

Timing groups are not a significant feature in this invention and may be any of the groups known in the art such as those shown in U.S. Pat. No. 5,457,004. Some examples of embodiments of the high dye-yield coupler synthesizable by this process are shown in U.S. Pat. Nos. 5,447,819 and 5,457,004. Other examples of couplers that can be formed using the process oil the invention are as follows Inv-1

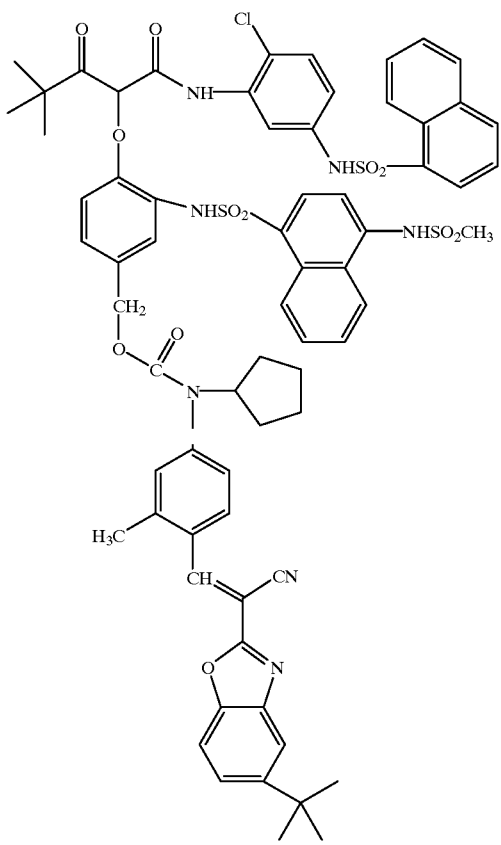

Inv-2
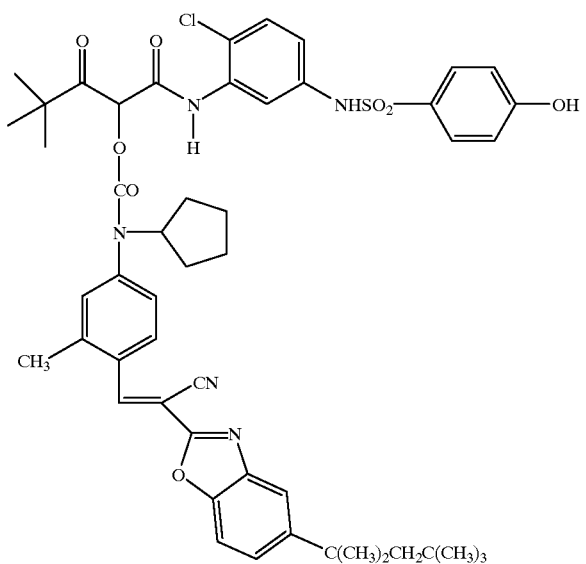
Inv-3
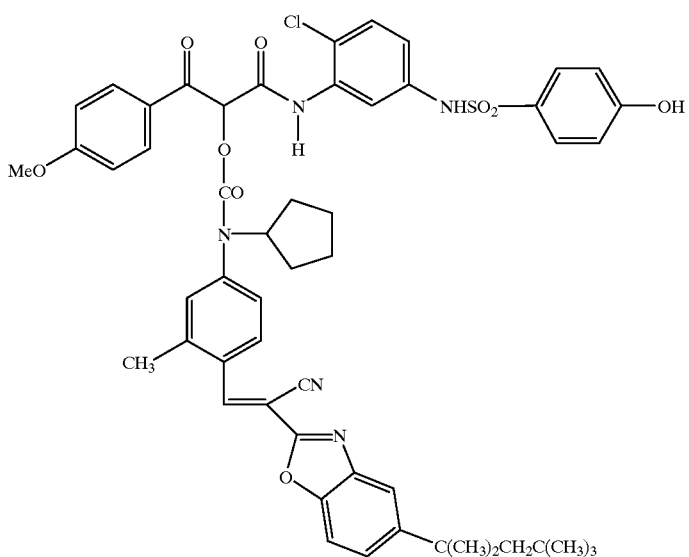

-continued
Inv-4
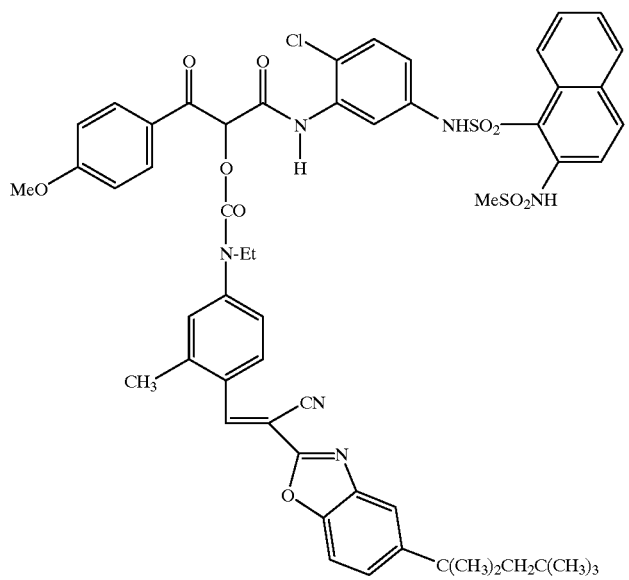
Inv-5
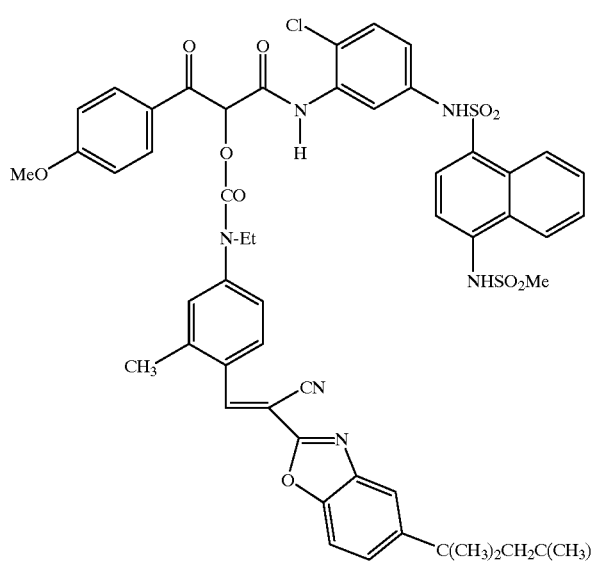

-continued
Inv-6
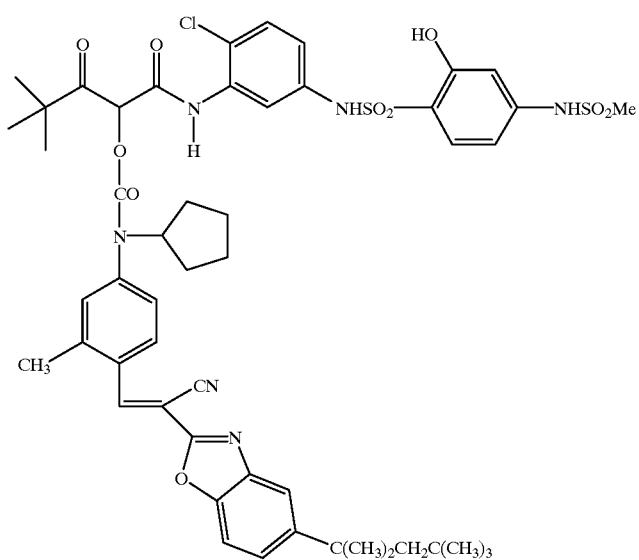
Inv-7
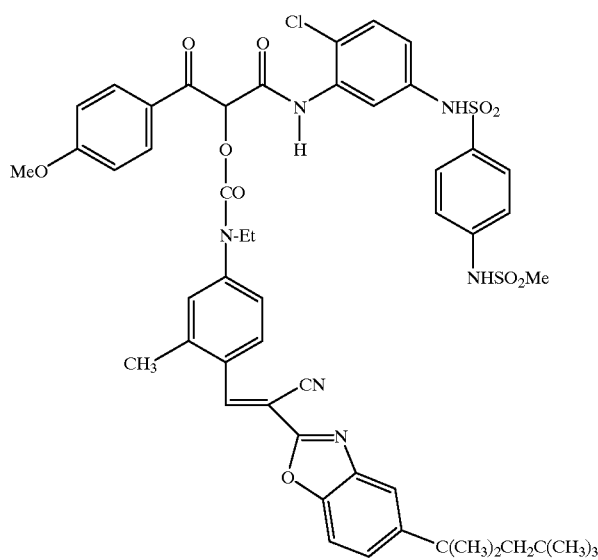

Inv-8
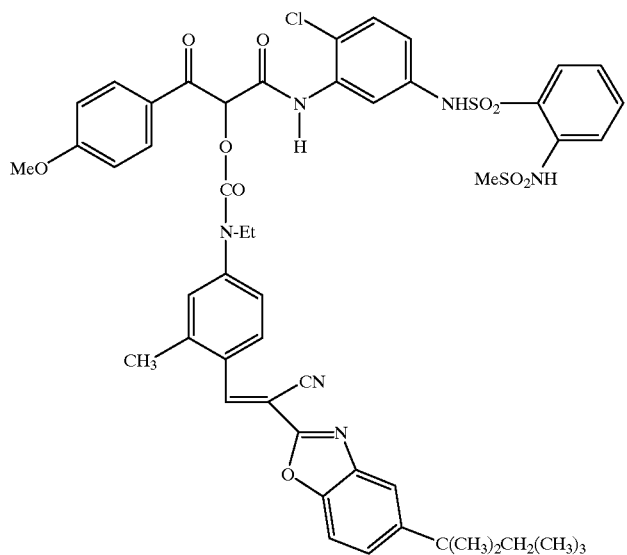
Inv-9
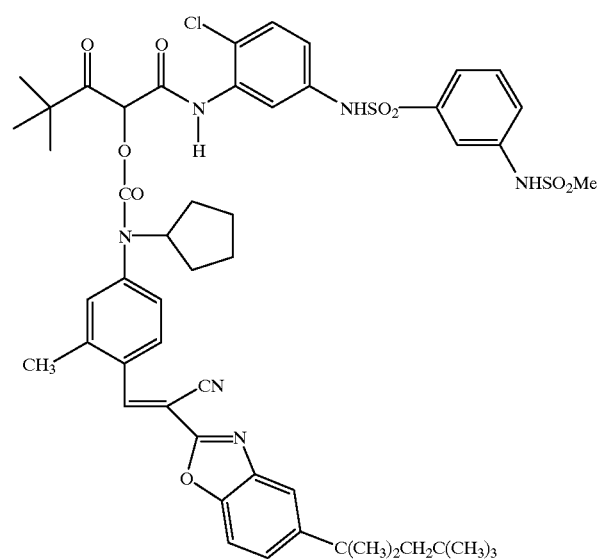

-continued
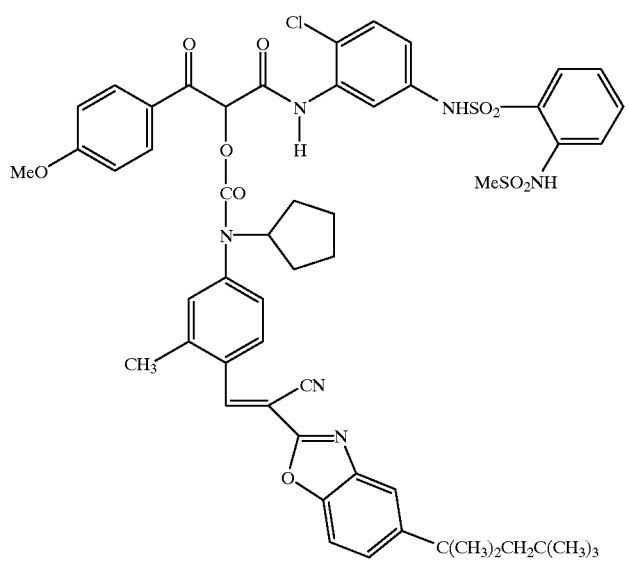
Inv-10
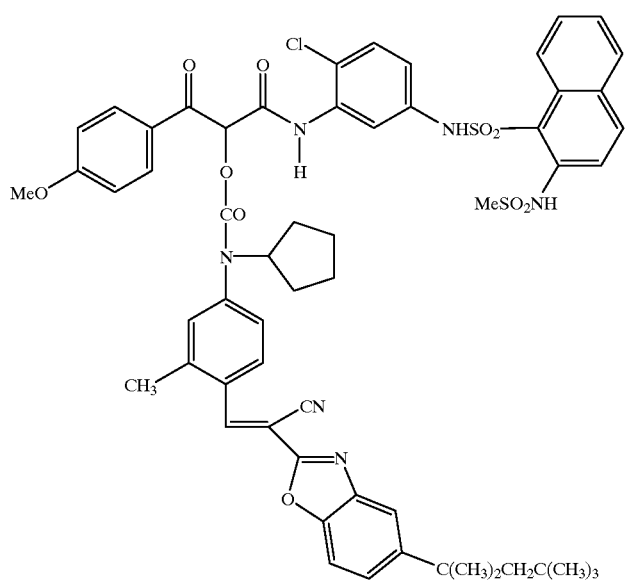
Inv-11

-continued
Inv-12
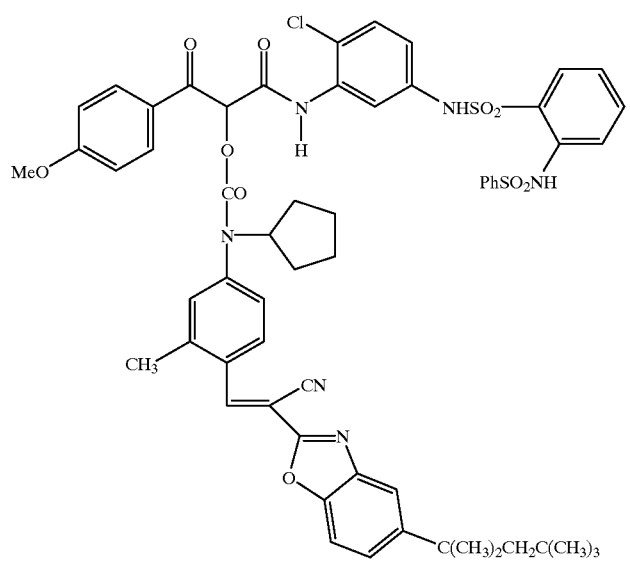
Inv-13
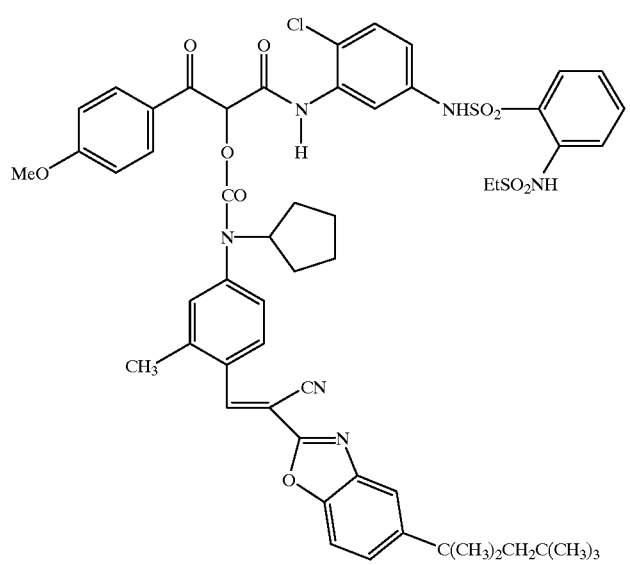

Inv-14
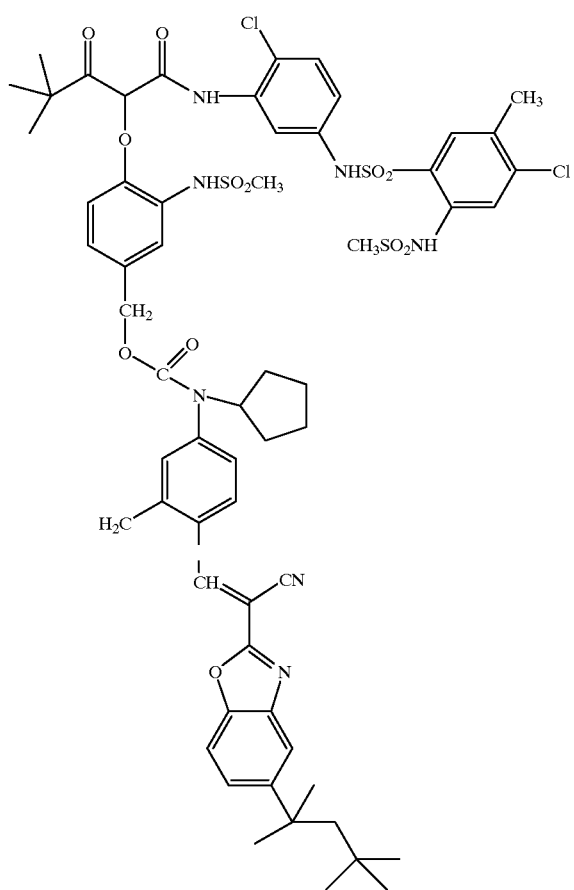
Inv-15
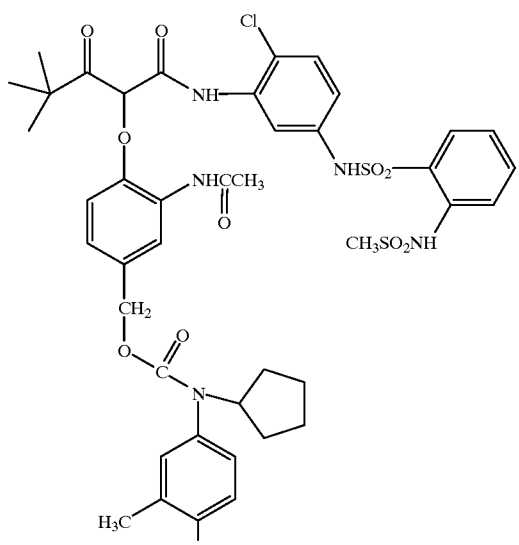

-continued
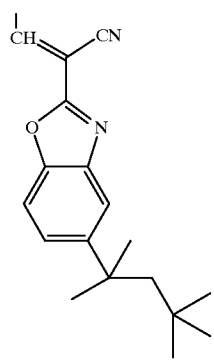
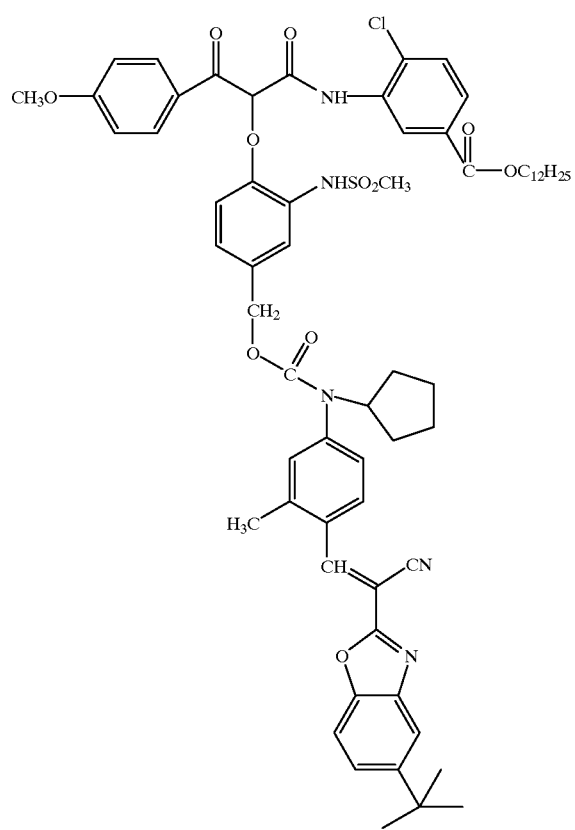
Inv-16

Inv-17
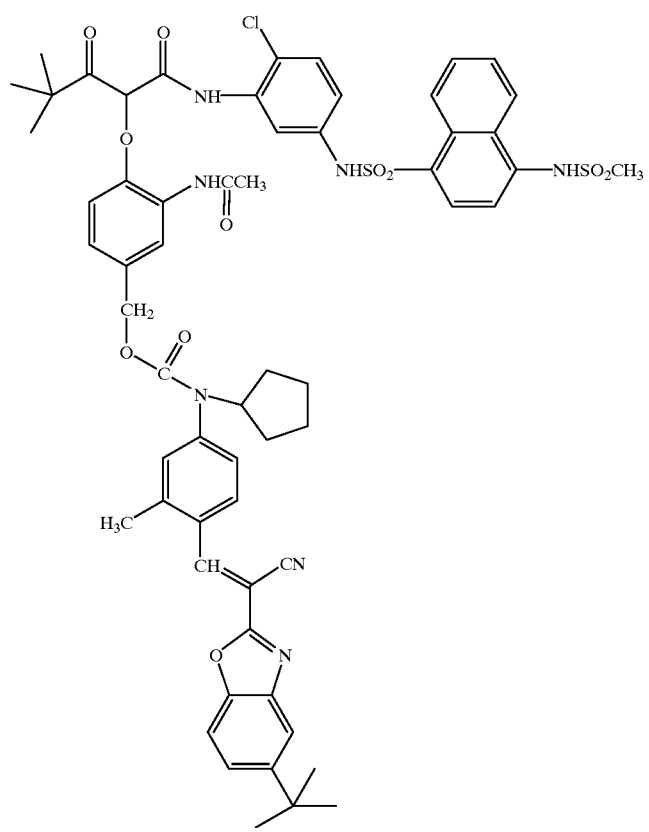
Inv-18
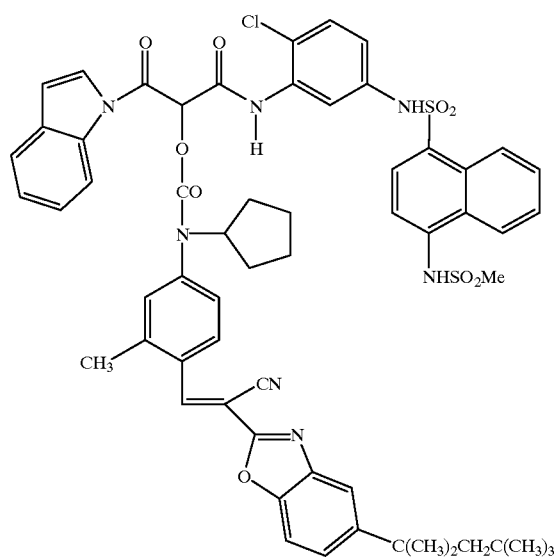

-continued
Inv-19
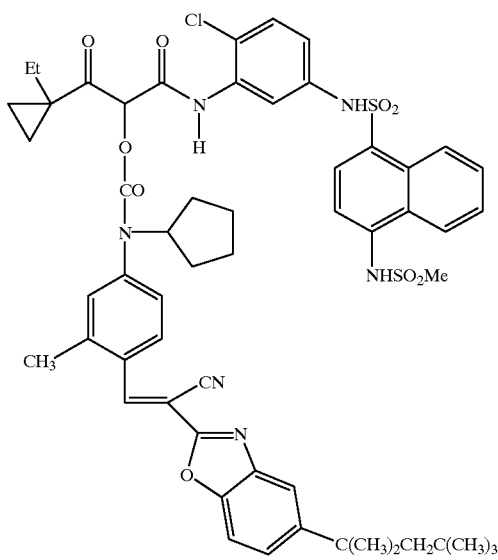
Inv-20
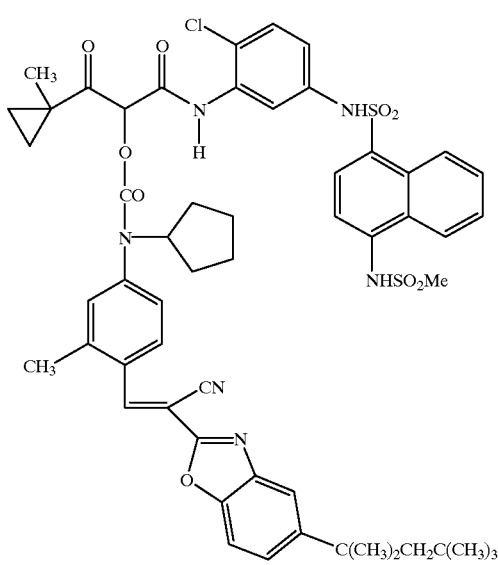

-continued
Inv-21
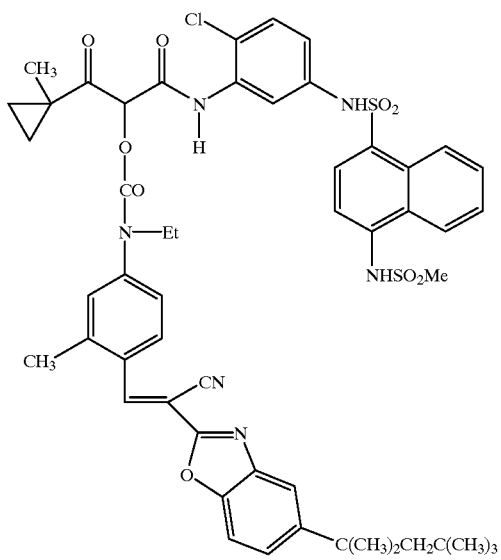
Inv-22
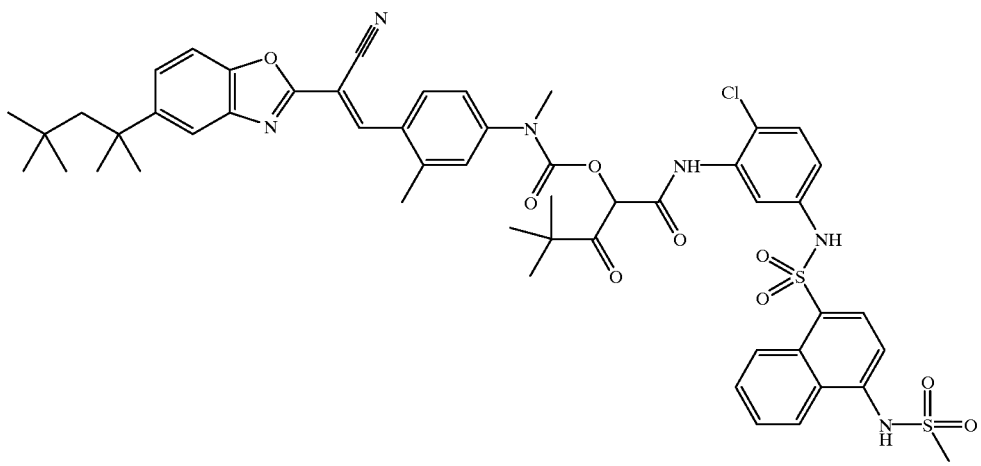
Inv-23
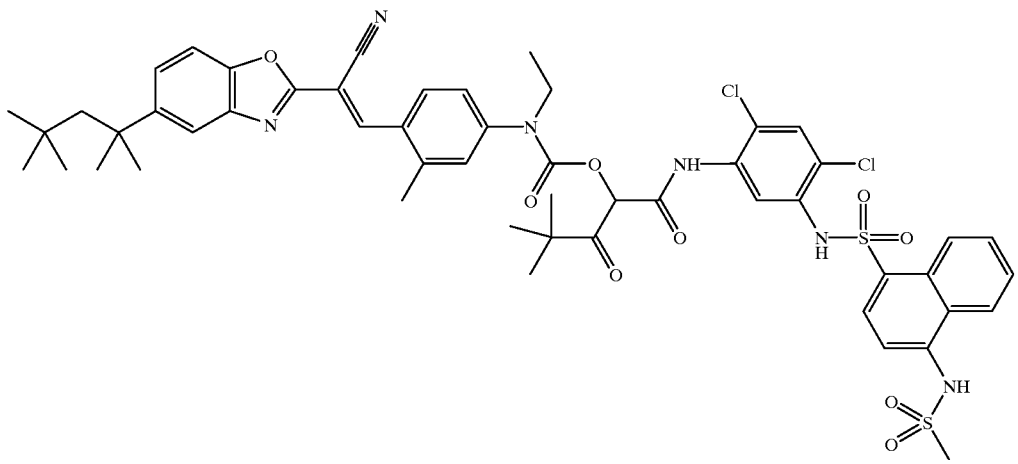

Inv-24
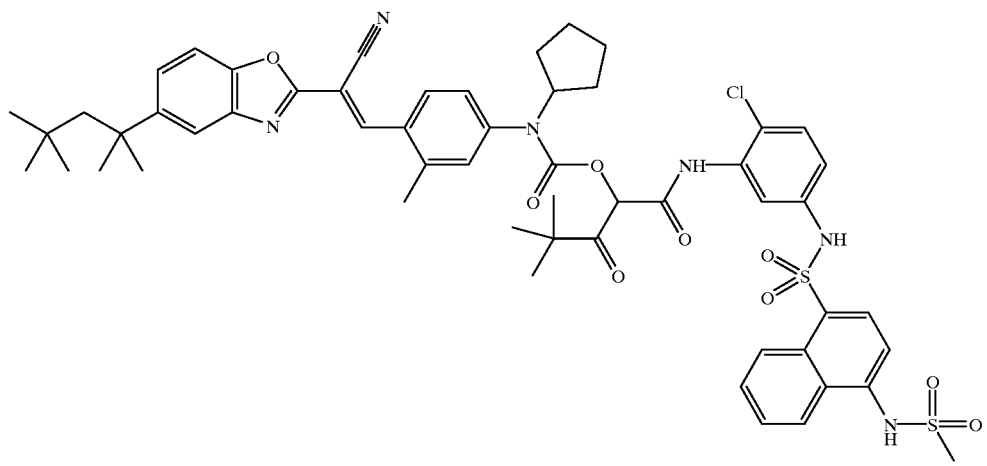
Inv-25
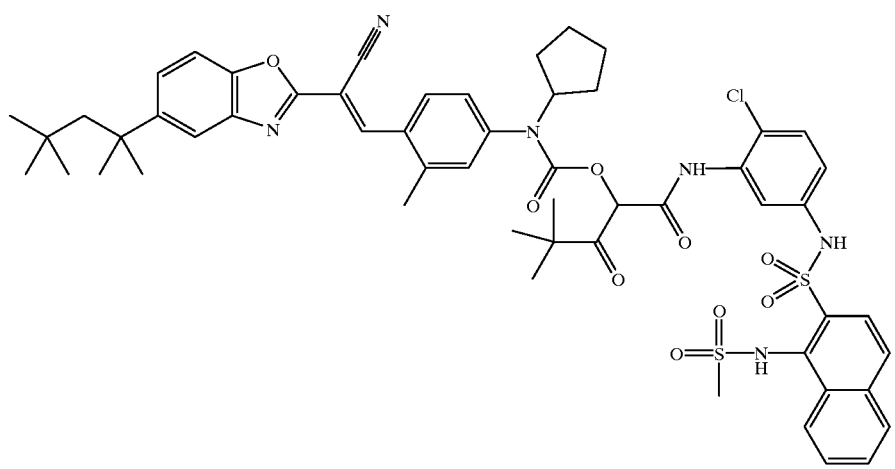
Inv-26
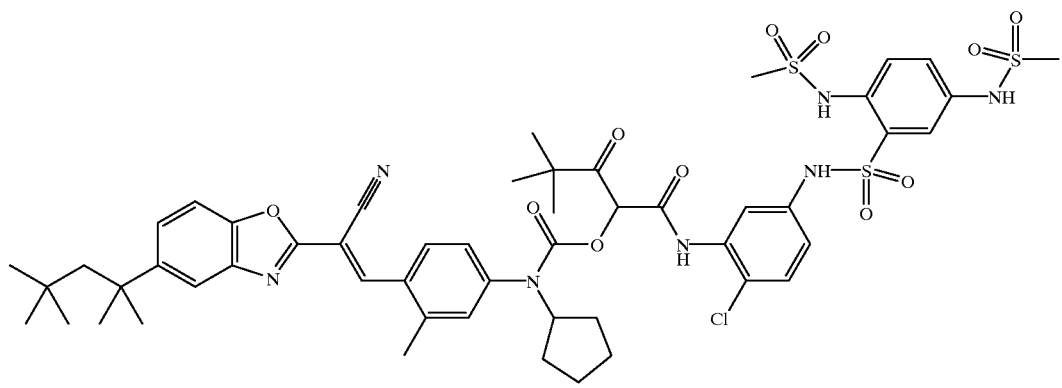

-continued
Inv-27
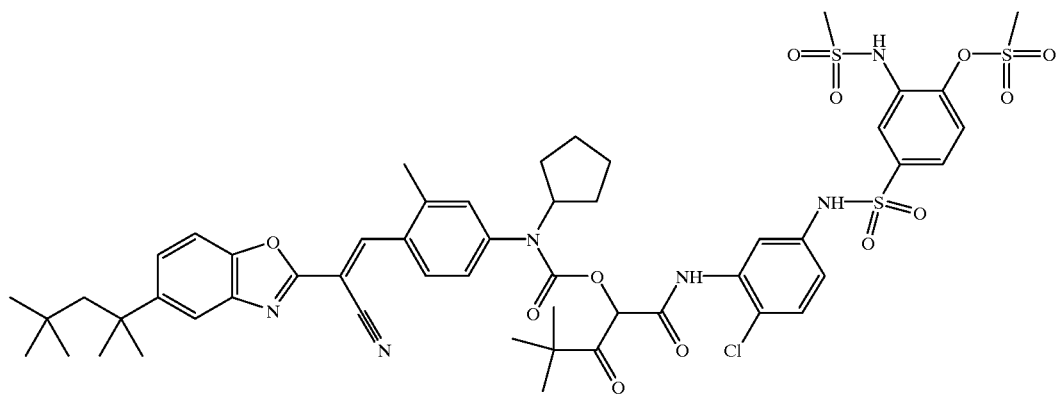
Inv-28
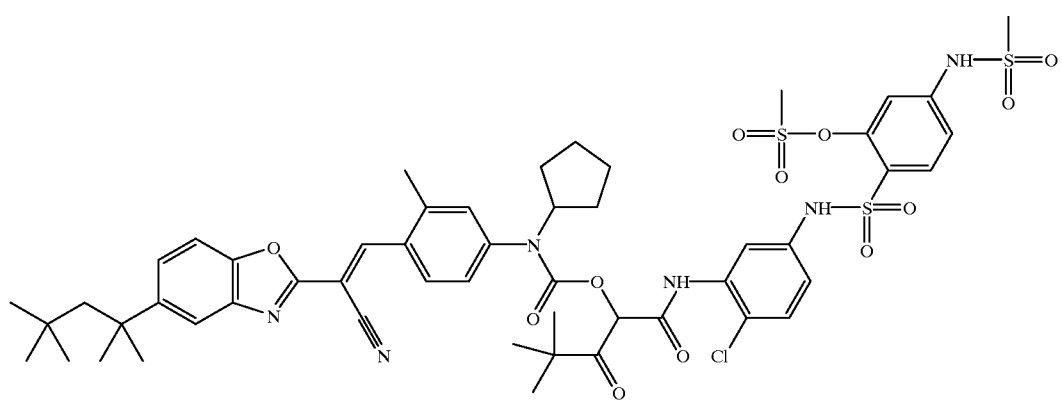
Inv-29
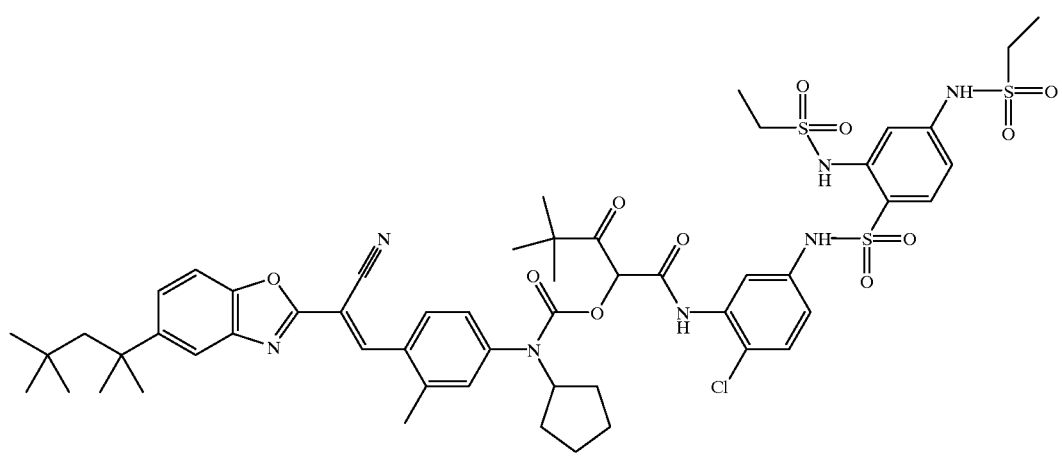

-continued
Inv-30
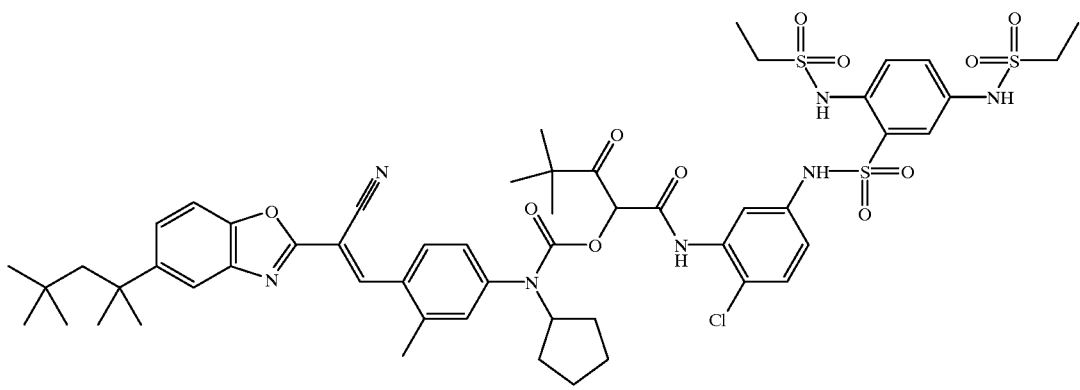
Inv-31
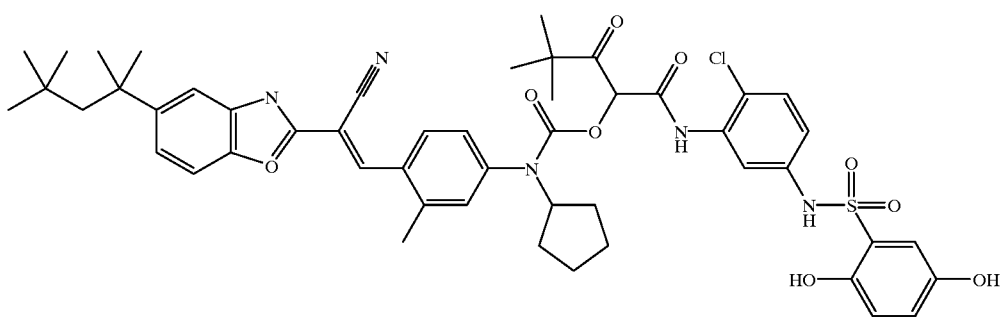
Inv-32
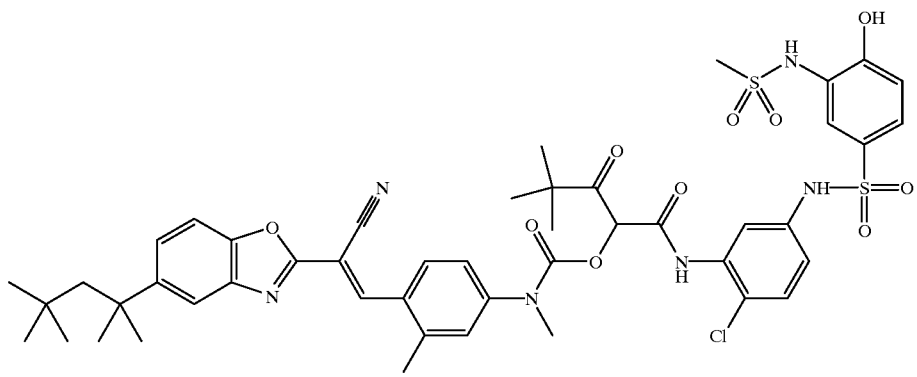
Inv-33
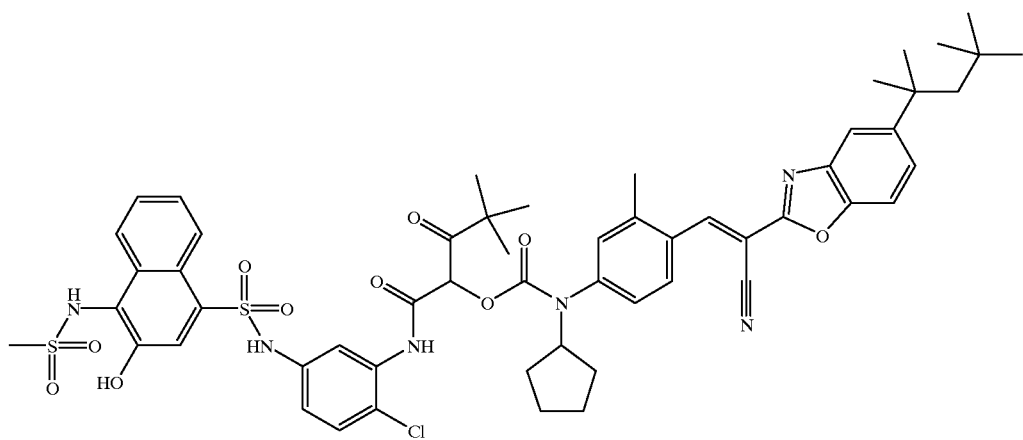

-continued
Inv-34
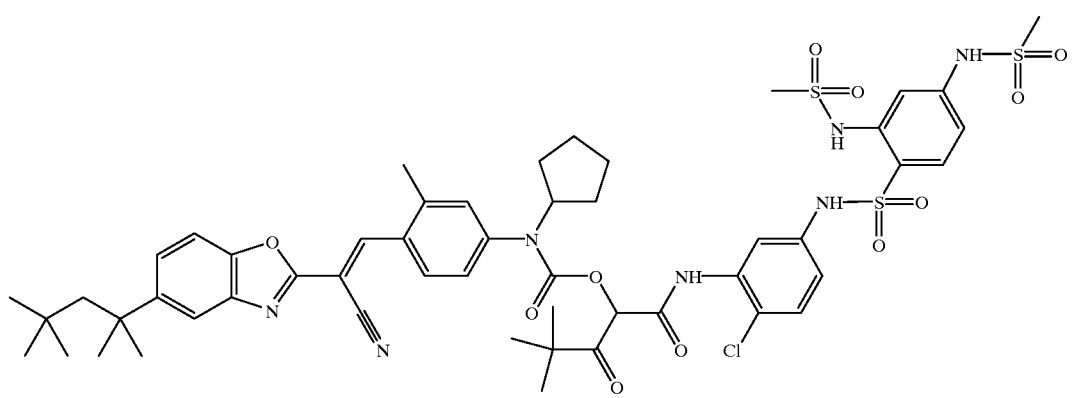
Inv-35
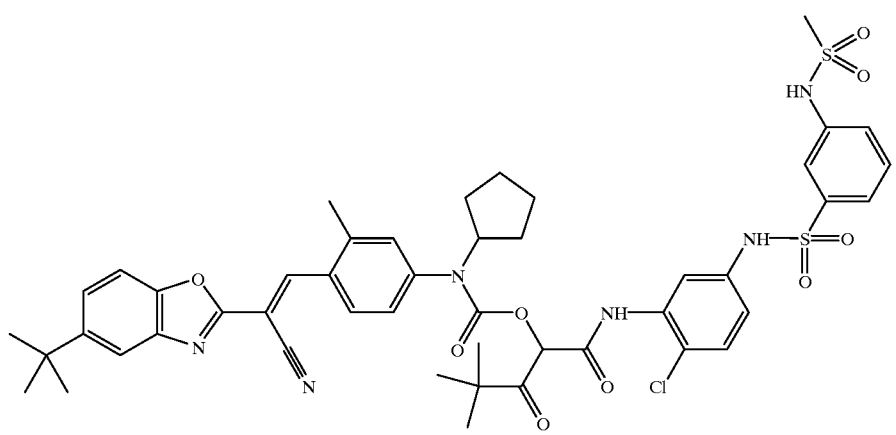
Inv-36
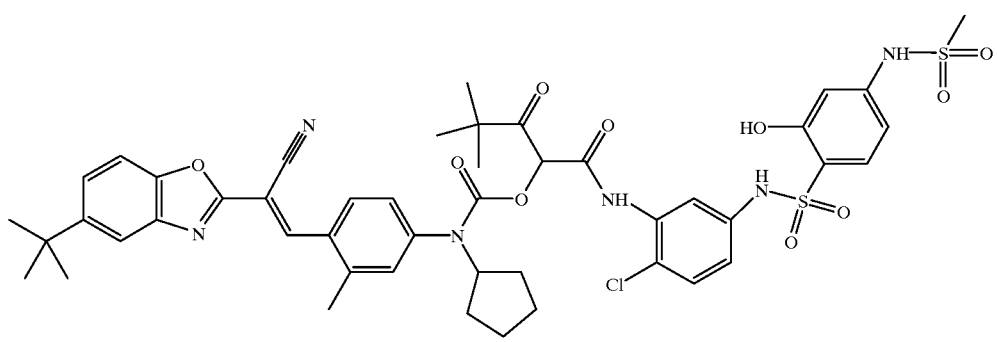

-continued
Inv-37
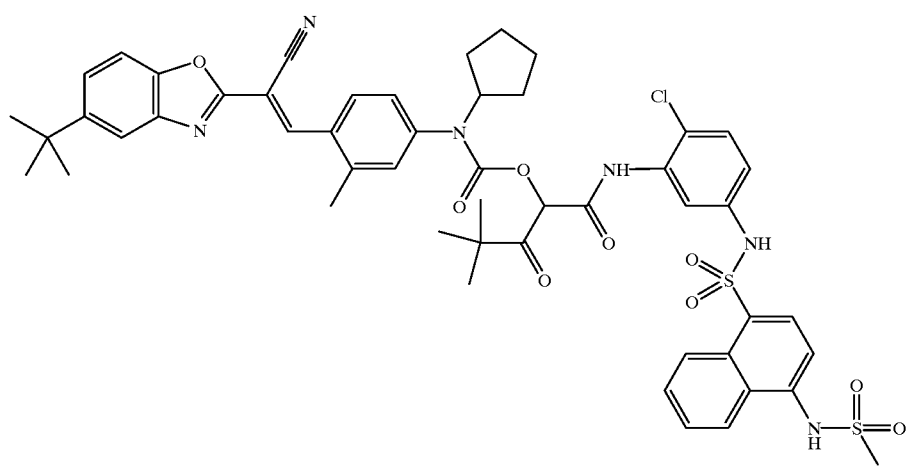
Inv-38
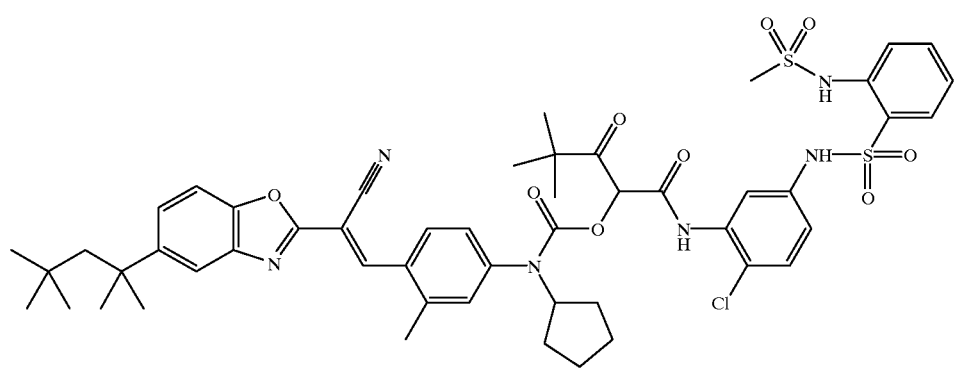
Inv-39
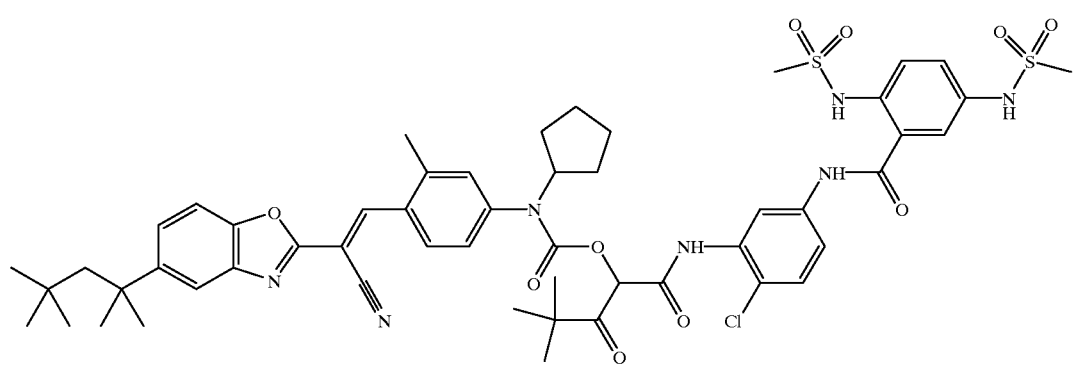
Inv-40
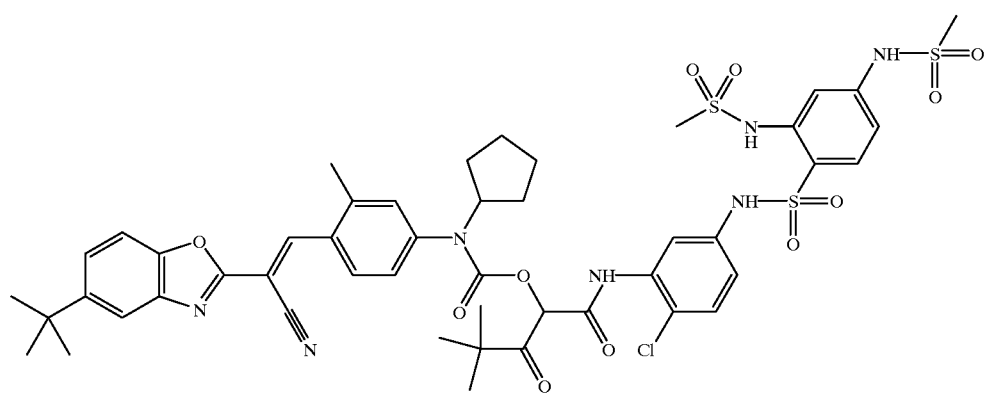

-continued
Inv-41
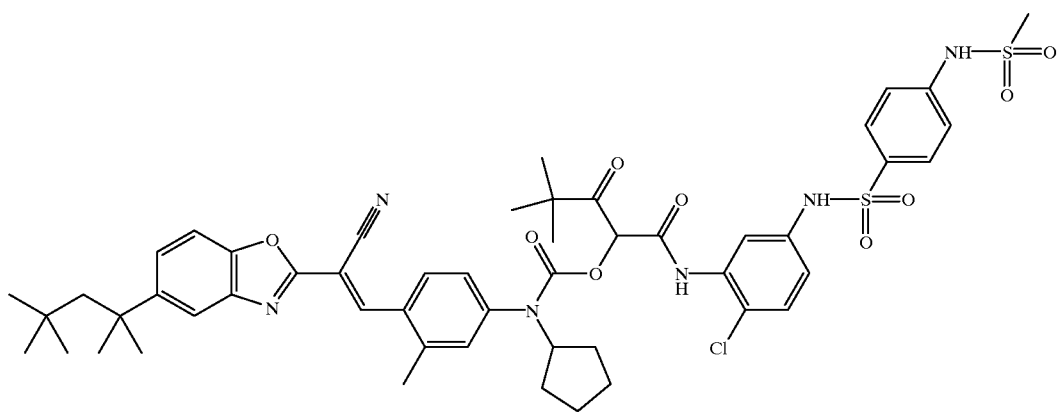
Inv-42
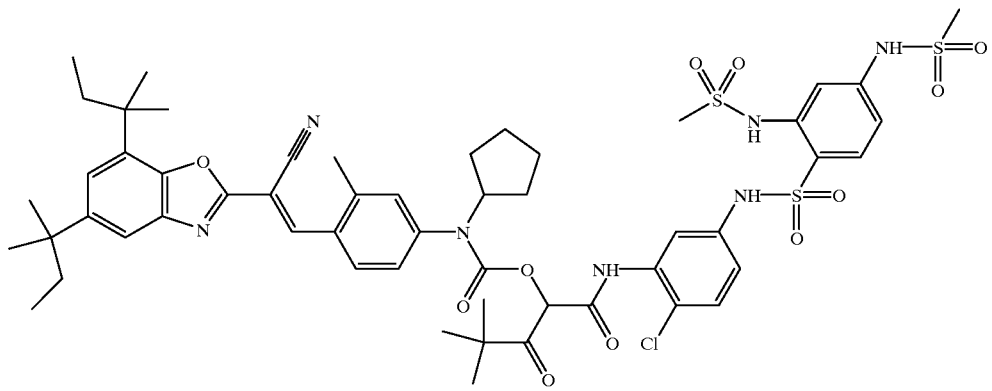
Inv-43
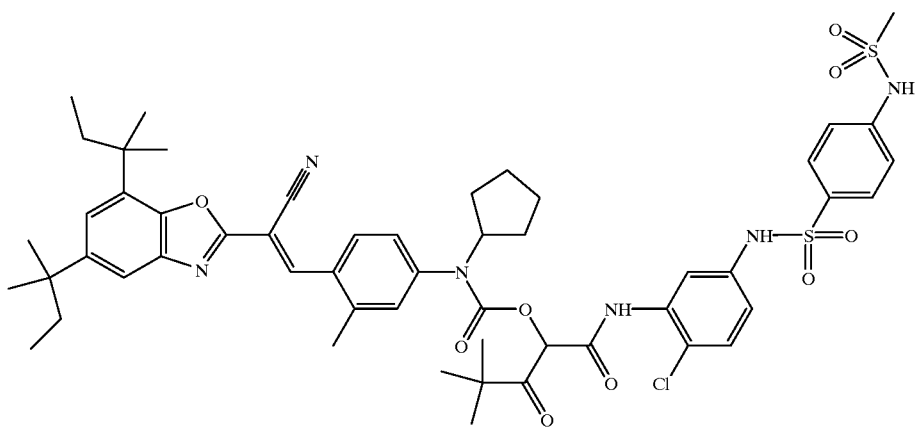

Inv-44
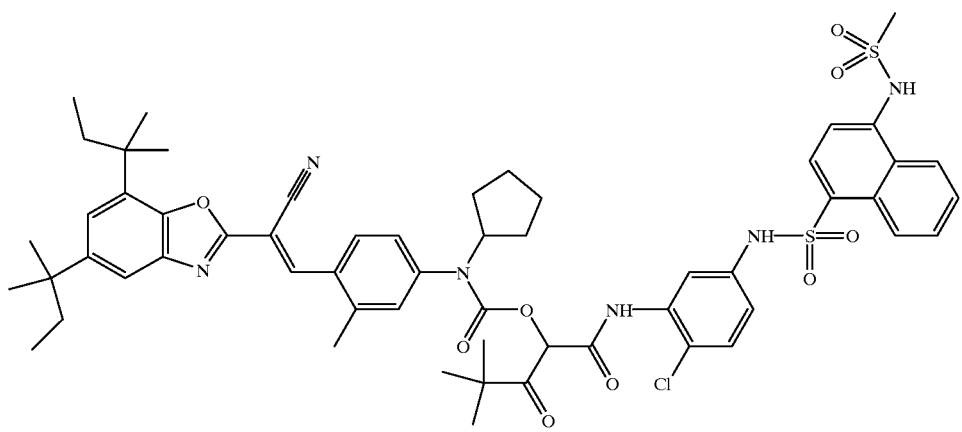
Inv-45
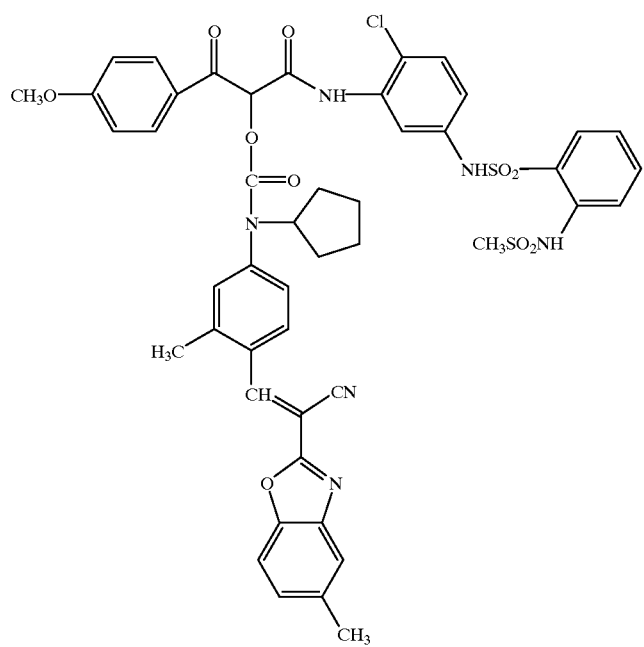
Inv-46
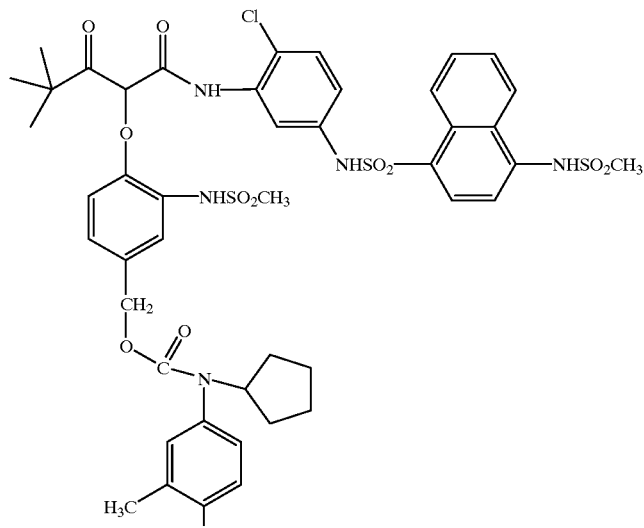

-continued

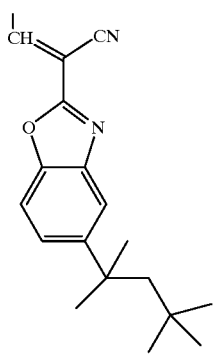

The use of intermediates of Formula I provides flexibility and simplicity in the preparation of high dye-yield couplers. Several small parts of couplers can be made separately and put together to build a complex coupler molecule. All of the reactions involved in making and using the intermediates are simple and efficient, and give high yield of products, so that the cost of manufacturing the couplers can be greatly reduced. The efficient high yield reactions allow combining intermediate steps without isolation which reduces cost and generates less waste.

As described in the preceding Summary of the Invention, the present invention relates to carbamyl chlorides of aminoarylcarbonyl compounds, intermediates for the preparation of high dye-yield couplers, process of making and using them, the high dye-yield couplers having the formula:

Formula II

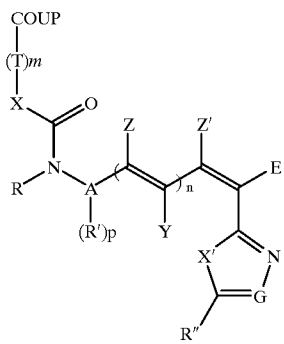

Thus, the present invention provides intermediates of Formula I which are parts of methine dye molecules, a process of making them and attaching them to a parent coupler-timing group piece of Formula IV first and forming the methine dye last with the rest of methine dye molecule of Formula IV to build high dye-yield couplers of Formula II.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. In the intermediates of Formula I, R is an alkyl group, such as alkyl containing 1 to 42, typically 1 to 22 carbon atoms. Representative substituted alkyl groups include branched alkyls, cyclic alkyls, arylalkyls, heterarylalkyls, or alkyls substituted with halogens or inert hetero atoms. Preferred branched alkyl groups are isopropyl, 2-methylpropyl, sec-butyl, 3-methylbutyl, 3-methyl-2-butyl, 3,3-dimethyl-2-butyl, 4-methyl-3-buten-2-yl, 2-pentyl, 3-pentyl, 4-methy-2-pentyl, 2-hexyl, 3-hexyl, 5-methyl-2-hexyl, 2-heptyl, 3-heptyl, 4-heptyl, 2-octyl, 5-nonyl, 2-undecyl, and the like. Preferred cyclic alkyl groups are cyclopropyl, cyclobutyl, cyclopentyl, cyclchexyl, 2-methylcyclohexyl, 4-methylcyclohexyl, 4-t-butylcyclohexyl, cycloheptyl, cyclooctyl, cyclononyl, cyclodecyl, cycloundecyl, cyclododecyl, and the like. Preferred arylalkyl groups are benzyl, 4-acet-amidobenzyl, 4-bromobenzyl, 4-butoxybenzyl, 4-butylbenzyl, 2-chlorobenzyl, 4-chlorobenzyl, 4-cyanobenzyl, 2,5-dimethoxybenzyl, 4-dimethylaminobenzyl, 4-ethylbenzyl, 2-methoxybenzyl, 4-methoxybenzyl, 4-methylbenzyl, 2-nitrobenzyl, 3-nitrobenzyl, 4-nitrobenzyl, 4-octylbenzyl, 3,4,5-trimethoxybenzyl, 1-naphthylmethyl-, 9-anthracylmethyl, 1-phenylethyl-, 2-phenylethyl, 1-phenylpropyl, 1-phenylbutyl, 2-methyl-1-phenylpropyl, 3-methyl-1-phenylbutyl, 1-phenyloctyl, 1-(4'-bromophenyl)ethyl, 1-(4'-chlorophenyl)ethyl, 1-(2', 4'-dichlorophenyl)ethyl, 1-(3', 4'-dimethoxyphenyl)ethyl, 1-(2', 5'-dimethylphenyl)-ethyl, 1-(4'-methoxyphenyl)ethyl, 1-(4'-methylphenyl)ethyl, 1-(1-naphthyl)ethlyl, 1-(2-naphthyl)ethyl, and the like. Preferred heteroarylalkyl groups are 2-furylmethyl, 2-pyrrolemethyl, 2-pyridylmethyl, 2-thienylmethyl, 1-(2-furyl)ethyl. 1-(3-pyridyl)ethyl, 1-(4-pyridyl)-ethyl, 1-(2-thienyl)ethyl, and the like. Preferred alkyls substituted with halogens or inert hetero atoms include 1-chloro-2-propyl, 2-chloro-1-phenylethyl, 2-bromo-1-phenylethyl, 2-bromo-1-(4'-nitrophenyl)ethyl, 2-bromo-2-phenyl-1-phenylethyl, 1-methoxy-2-propyl, 1-methylmercapto-2-propyl, 1-dimethylamino-2-propyl, 2-methoxy-1-phenylethyl, 2-methylmercapto-1-phenylethyl, 2-dimethylamino-1-phenylethyl, 2-methoxy-1-(4'-nitro-phenyl)ethyl, 2-methylmercapto-1-(4'-nitrophenyl)ethyl, 2-dimethylamino-1-(4'-nitro-phenyl)ethyl, 2-methoxy-2-phenyl-1-phenylethyl, and the like.

A is a substituted or unsubstituted aryl (including heteroaryl) ring group containing up to three optional substituents R'. Suitably, A is a phenyl, naphthyl, or thiazole ring group. Each R' is independently an alkyl group which may form a ring with Z or Z' and p is an integer from 0 to 3. One or more R' substituents may be present which preferably include alkyl groups of from 1 to 5 carbon atoms such as methyl, ethyl, propyl, or isopropyl.

Each Z, Y, and Z' is independently hydrogen or a substituent. Preferred Z substituents are alkyl groups which may form a ring with R'. Y substituents preferably include alkyl groups of from 1 to 5 carbon atoms such as methyl, ethyl, propyl, or isopropyl. Preferred Z' substituents are also alkyl groups which may form a ring with R' when n=0.

n, which represents the number of conjugated vinyl groups and affects the hue of the dye, is 0, 1, or 2.

Preparation of a carbamyl chloride by phosgenation of an amino compound is a well known reaction. However, phosgenation of the sterically hindered amine in branched or bulky aminocarbonyl compounds is difficult. When they are reacted with phosgene, not only is the amine converted to carbamyl, but the carbonyl oxygen is also replaced by two chlorine atoms. This problem can be circumvented by protecting the carbonyl function in the form of a Schiff base prior to phosgenation. After the phosgenation of protected aminoarylcarbonyl compounds, the protecting group can be readily removed by dilute acid hydrolysis. The following scheme illustrates the protection, phosgenation, and deprotection of the aminoarylcarbonyl compounds:

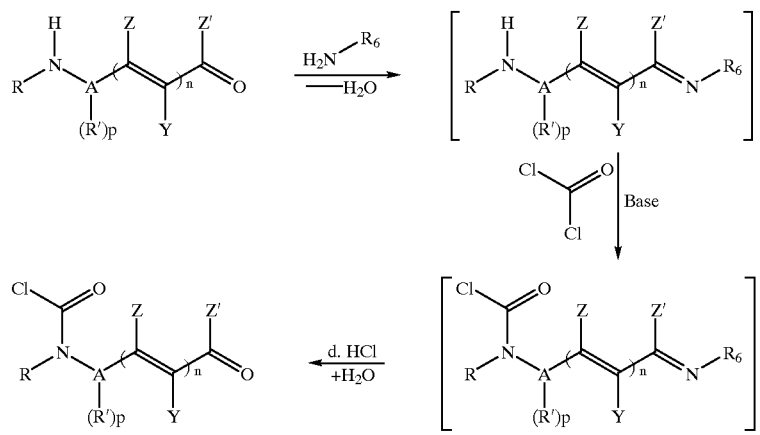

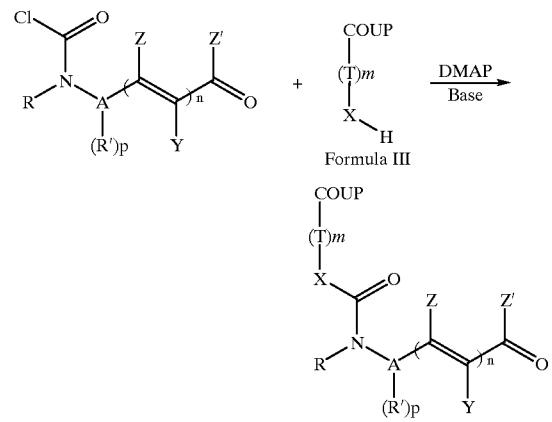

The Schiff base formation of a carbonyl compound with a primary amine is well known in the literature. It is preferably done by azeotropic removal of water formed in the reaction that proceeds smoothly in the presence of an acid catalyst. Suitable primary amine examples for this Schiff base formation are t-butylamine, cyclohexylamine, and t-octylamine.

The Schiff base formed has limited stability, thus is used directly, without isolation, in the phosgenation reaction. The phosgenation reaction is Eo preferably done with a tertiary amine organic base such as triethylamine or 2,6-lutidine. The carbamyl chloride of the hindered amine is quite stable and survives dilute acid hydrolysis of the Schiff base.

All the conversions are simple and efficient such that they can be done in one pot giving high quality and yield of product.

The carbamyl chloride of the aminoarylcarbonyl compounds can be readily and efficiently attached to a wide variety of coupler-timing group pieces of Formula III. The following scheme illustrates the reaction:

The reaction is preferably done with an acyl transfer agent such as 4-N,N-dimethylaminopyridine (DMAP) to activate the carbamyl chloride and a strong organic base to ionize the proton of —X—H on coupler-timing, group piece. Suitable strong organic bases for this reaction are triethylamine, DBN, Dabco, and DBU.

In the coupler-timing group piece of Formula III, COUP is the parent portion of a coupler that is capable of coupling with oxidized developer to form a first dye. T is a timing group which, as indicated by the value range for m of from 0 to 2, may be absent or represent one or two such timing groups. Such couplers with or without timing groups are well known and described in U.S. Pat. No. 5,457,004 and references cited therein.

The methine dye formation can be done via condensation reaction of the carbonyl portion of coupler-timing group-aminoarylcarbonyl compounds with an active methylene portion of the rest of the dye molecule of Formula IV to form the methine dye of Formula II.

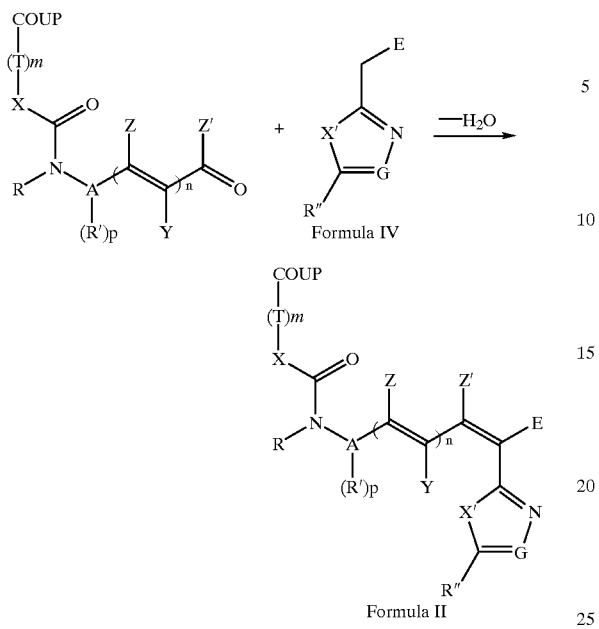

Formula IV

Formula II

This condensation is also preferably done by azeotropic removal of water formed in the reaction which proceeds smoothly in the presence of a catalyst such as piperidine/acetic acid.

The following are examples that further illustrate the invention. These examples compare the synthesis of Inv-5 via the route which incorporates the reaction of the carbamyl chloride of the aminoarylcarbonyl intermediate (Formula I of invention) with the hydroxy substituted COUP group) (Example 1: D+F→G; 89% yield) vs the comparison route (Example 2) which utilizes the reaction of the carbamyl chloride of the preformed methine dye with the hydroxy substituted COUP group (Example 2: D+H→I; 31% yield). The 89% yield observed in Example 1 for D+F (Formula I of invention) →G is typical of yields for this reaction even when R of Formula I is a larger and preferred branched alkyl group such as isopropyl or cyclopentyl in place of the less bulky ethyl group shown in Example 1. However, for the synthesis exemplified by the comparison route (Example 2), when the amino alkyl group of the carbamyl chloride of the preformed methine dye (analogous to R of Formula I) is larger than ethyl, yields become much less (usually<5%) than the 31% yield observed in Example 2 where the alkyl group is ethyl.

Examples 1 and 2 illustrate that the synthesis of Inv-5 via the Example 1 route which incorporates the intermediate of this invention (Formula I) is much more efficient than the comparison route (Example 2) which utilizes the carbamyl chloride of the preformed methine dye. This efficiency advantage is even greater when the alkyl amino group (R of Formula I) is the preferred isopropyl or cyclopentyl group instead of ethyl.

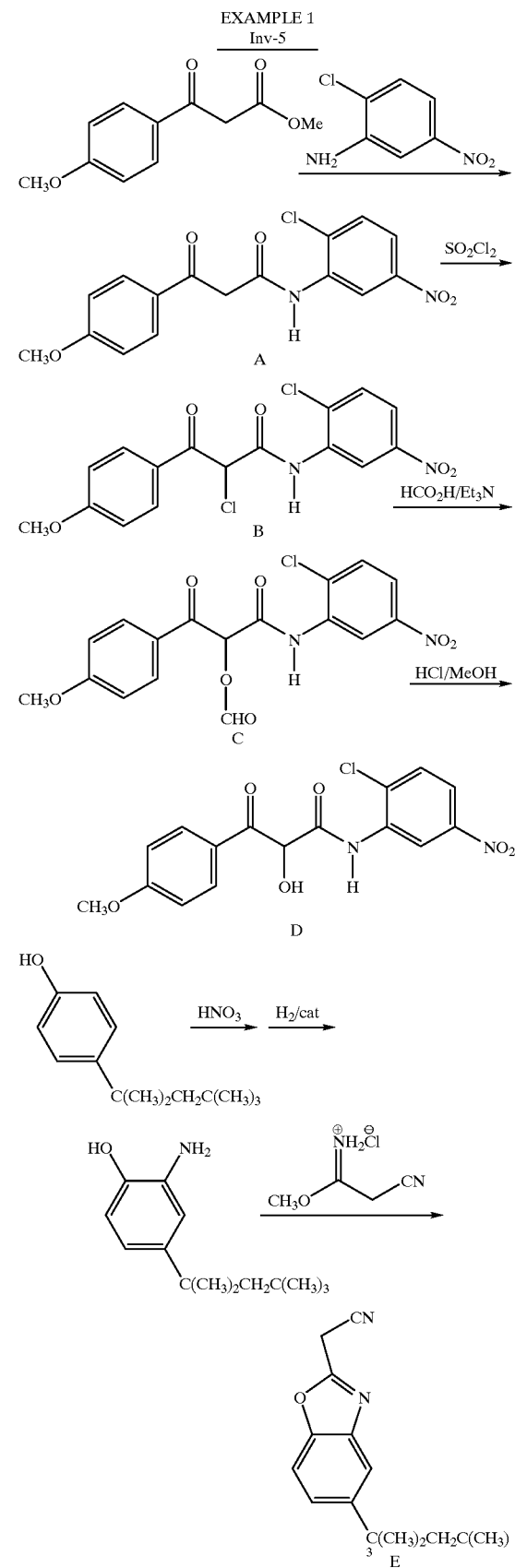

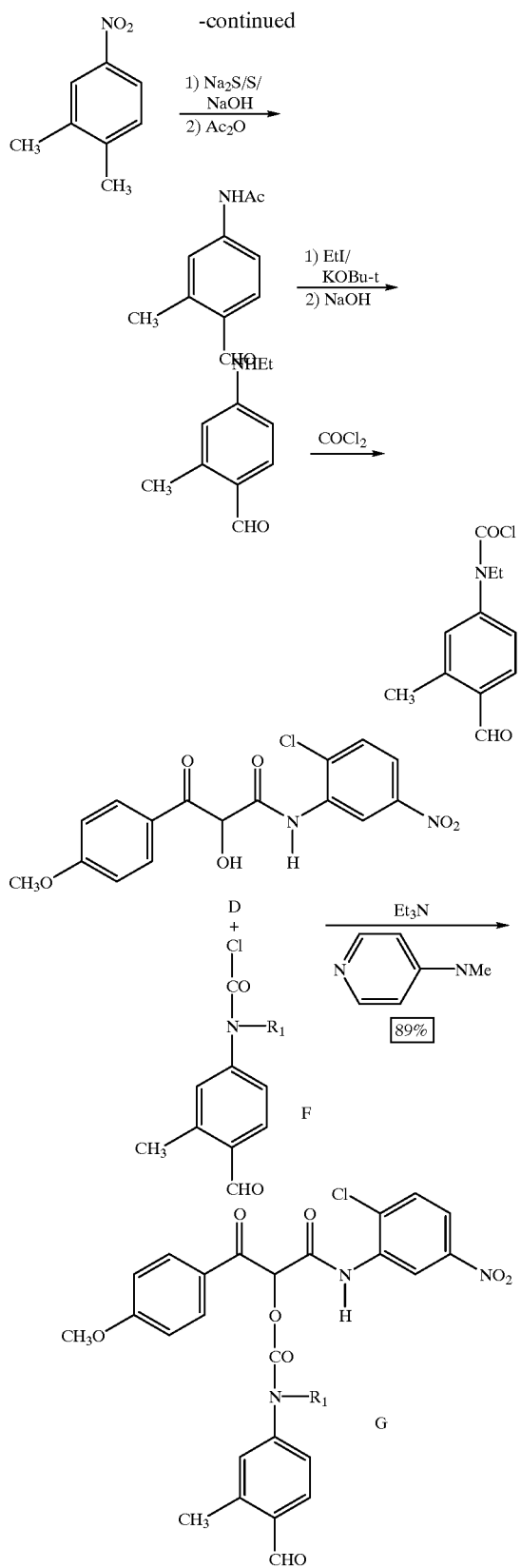
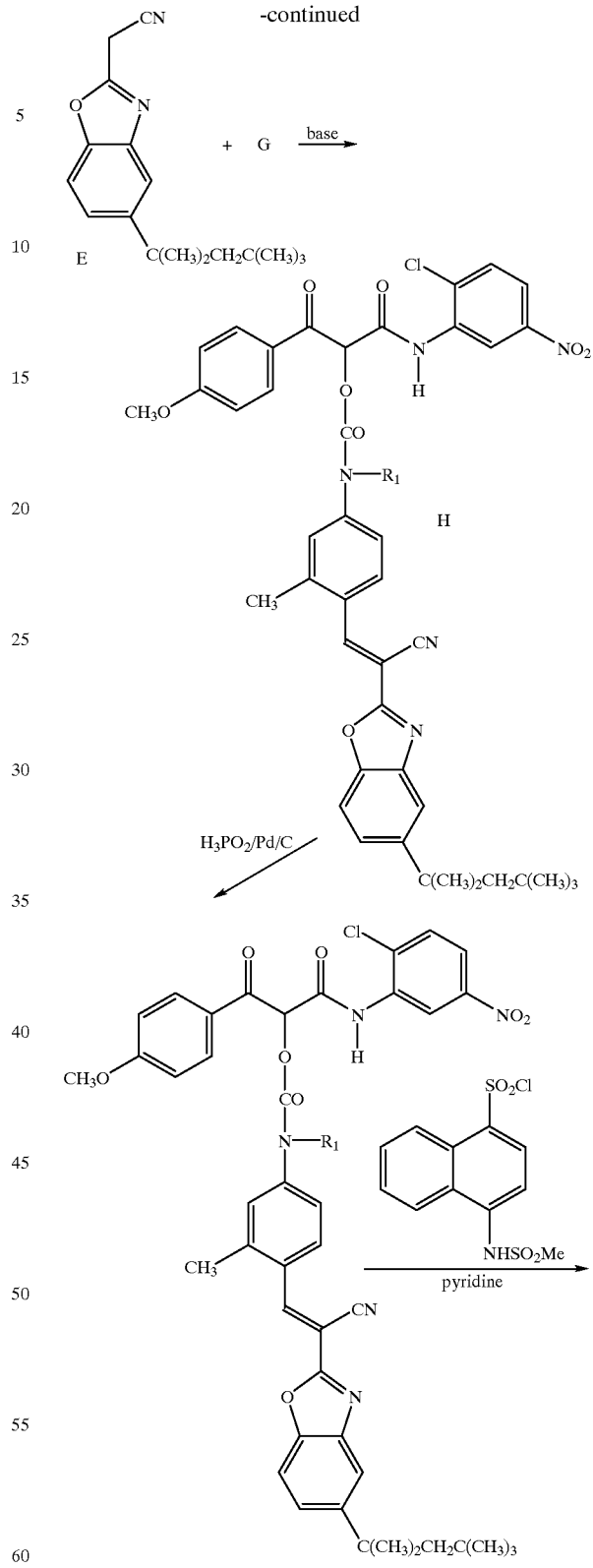

EXAMPLE 2
Inv-5 via Comparison Route
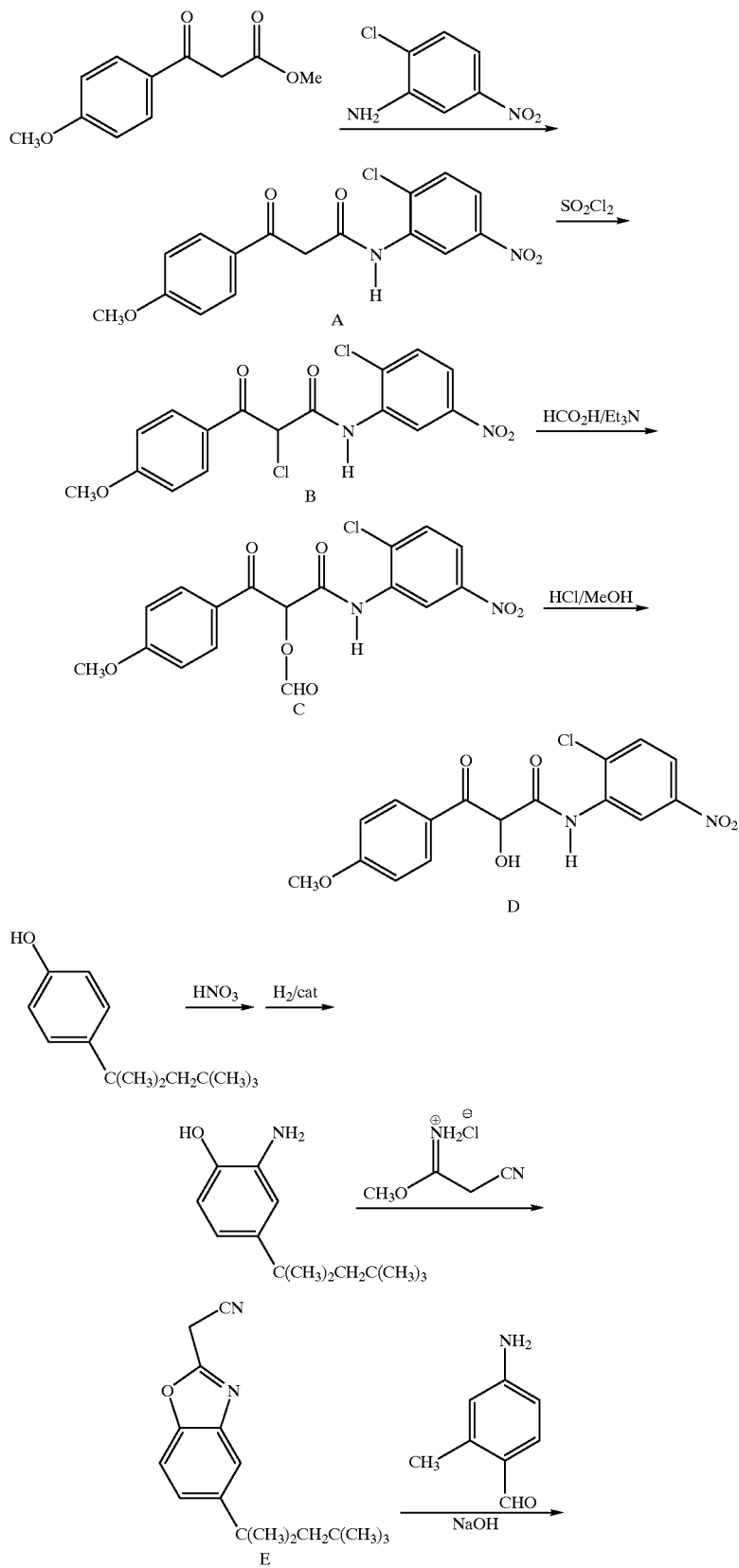

-continued
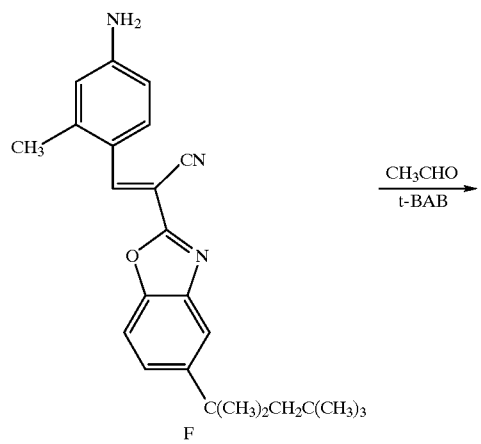
F
$\xrightarrow{\text{CH}_3\text{CHO}}_{\text{t-BAB}}$
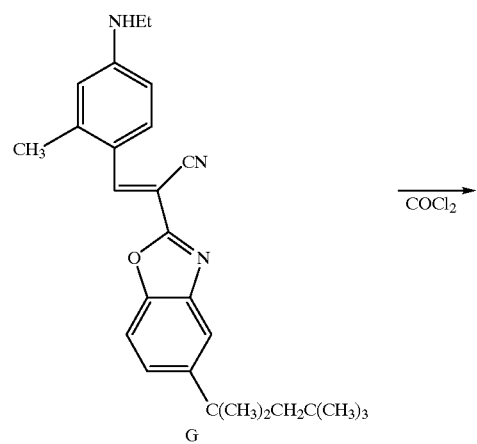
G
$\xrightarrow{\text{COCl}_2}$
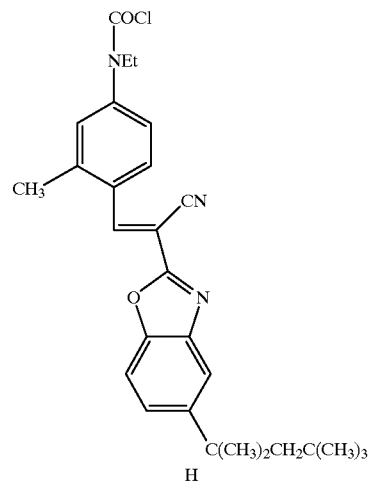
H

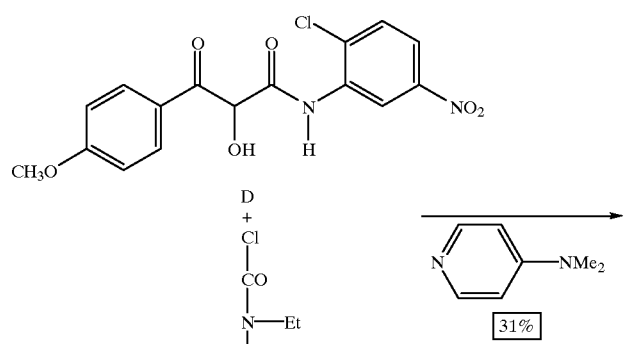
D
+
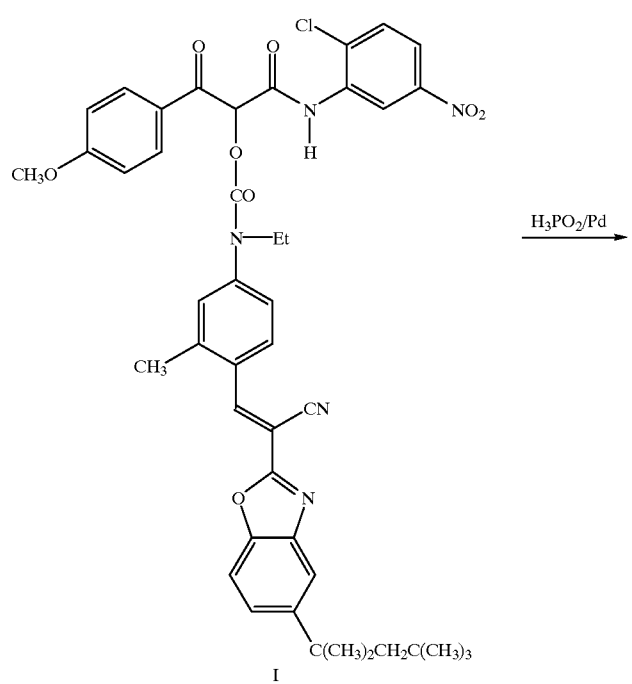
H
I
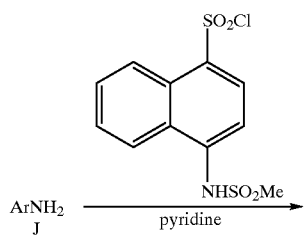
ArNH₂
J — pyridine →

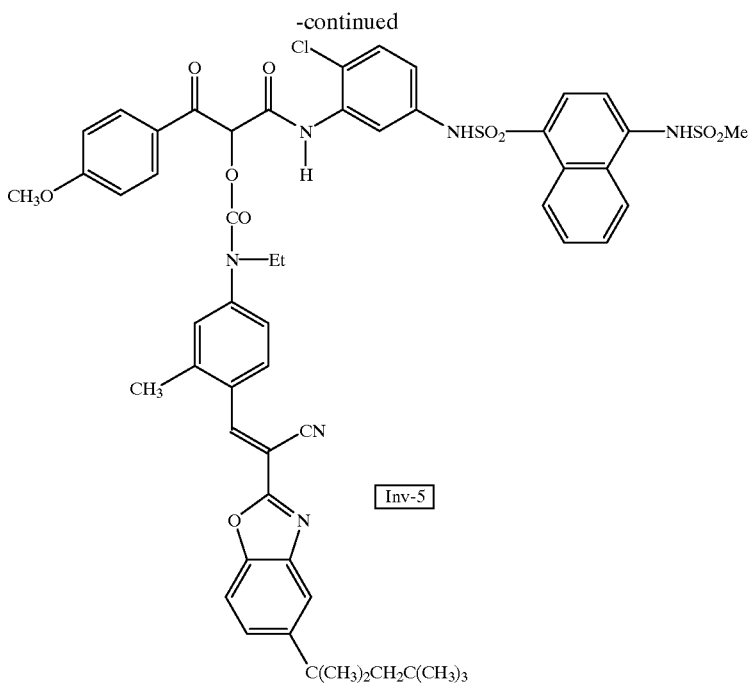

Inv-5

The following are the synthetic procedures for Example 1. These are typical procedures for the synthesis of high dye yield yellow couplers using the common intermediate of Formula I.

A mixture of sodium hydroxide (24 g, 0.6 mole), sodium sulfide nonahydrate (36 g, 0.15 mole), elemental sulfur powder (12.6 g, 0.4 mole), 4-nitro-o-xylene (45.4 g, 0.3 mole), tetrabutylammonium bromide (4.8 g, 0.015 mole), isopropyl alcohol (100 ml), and water (300 ml) was heated under reflux for 4 hr. A total of 270 ml of aqueous isopropyl alcohol was distilled from the mixture before cooling to room temperature. An orange gummy solid separated from the aqueous sulfide solution. The aqueous layer was decanted and the gum was washed once with about 10 ml of water. The gum was stirred mechanically while acetic anhydride (60 ml) was added; the temperature was controlled with a cool water bath. The mixture was then heated to about 50° for 30 min to complete the acetylation. After cooling to rt the mixture was diluted with water to precipitate the crude 2-methyl-4-acetamidobenzaldehyde product. The crude product was dissolved in a boiling mixture of heptane (200 ml), propyl acetate (100 ml), and water (100 ml) and then cooled to precipitate solid product. After filtration, this product was recrystallized once from ethanol:water (50 ml: 200 ml) and again from boiling propyl acetate (150 ml) with cooling in ice water before filtering off and drying the purified product (30.6 g, 53%).

A mixture of purified 2-methyl-4-acetamidobenzaldehyde (9.6 g, 0.054 mole), ethyl iodide (10 ml, 0.125 mole), and 50 ml of tetrahydrofaran was warmed to about 300 with stirring under a nitrogen atmosphere. Solid potassium t-butoxide (6.25 g, 0.056 mole) was added and the mixture was stirred for 2.5 hr at 30°. The mixture was concentrated under vacuum at 50° on a rotary evaporator to a syrup. The syrup was dissolved in methanol (30 ml) before adding water (20 ml) and then sodium hydroxide (5 g, 0.125 mole) to the mixture. After heating the mixture to reflux temperature for 30 min, it was cooled to rt and water (120 ml) was added. Solid product precipitated on stirring over night. After filtering and drying, 5.1 g (58%) of 2-methyl-4-ethylaminobenzaldehyde was obtained.

A mixture of methyl-(4-methoxybenzoyl)acetate (97 g, 0.47 mole), 2-chloro-5-nitroaniline (72 g, 0.42 mole), and 500 ml of xylene was heated under reflux and a slow stream of nitrogen for 6 hr. The mixture was allowed to cool to rt and stirred overnight. The crystalline product which formed was filtered off, washed with ether, and dried to 124 g (85%) of coupler intermediate A.

Coupler intermediate A (34.9 g, 0.1 mole), 300 ml of dichloromethane, and 8.1 ml of sulfuryl chloride were mixed, stirred vigorously, and heated to reflux momentarily. The mixture was then stirred at rt for 2 hr while the solid dissolved as chlorination proceeded. The mixture was concentrated at reduced pressure to a solid which was slurried in ether, filtered, and dried to yield 36.6 g (95%) of chloro coupler intermediate B.

Triethylamine (40.5 ml) and formic acid (96%, 11 ml) were, mixed with 90 ml of acetonitrile and cooled to rt. The mixture was stirred while chloro coupler intermediate B (36.6 g, 0.0955 mole) was added. After 1 hr the mixture was diluted with 120 ml of 1N HCl and stirred while a precipitate formed. The solid was filtered off, washed with water, and air dried to 36 g of crude product. After crystallization from methanol/tetrahydrofuran, 28.9 g (77%) of pure coupler intermediate C was obtained.

Coupler intermediate C (28.9 g, 0.073 mole) was dissolved in 120 ml of tetrahydrofuran. Methanol (120 ml) and 12 ml of conc. HCl were added before raising the temperature of the mixture momentarily to 40° with a warm water bath. The mixture was then stirred at rt and seeded with product crystals after 5 min. Water (15 ml) was added after 20 min and again after 1 hr (50 ml). The thick suspension was filtered after 1.25 hr, washed with water, a little 50% aqueous methanol, and then ether before drying to 22.5 g (84%) of hydroxy coupler intermediate D.

Phosgene (172 ml of 2M toluene solution, 0.344 mole) was added slowly to a cold (0°) solution of 2-methyl-4-ethylaminobenzaldehyde (38.6 g, 0.237 mole), lutidine (46 ml, 0.4 mole), and propyl acetate (260 ml). The mixture was allowed to warm to rt and then stirred for 30 min. The reaction mixture was washed with aqueous HCl and then with half-saturated brine, dried over $MgSO_4$, and concentrated to 61.5 g of crude oily carbamyl chloride intermediate F ($R_1$=Et).

A portion (38.2 g, 0.14 mole) of crude carbamyl chloride F ($R_1$=Et) was combined with hydroxy coupler intermediate D (49.6 g, 0.136 mole), 4-dimethylaminopyridine (DMAP, 1.7 g, 0.014 mole), triethylaminc- (29 ml, 0.2 mole), and propyl acetate (170 ml) under nitrogen atmosphere and stirred mechanically at rt for 1 hr. After washing the reaction mixture once with cold 1N HCl and then with water, drying over $MgSO_4$, and filtering through a small pad of silica gel, it was concentrated to a thick syrup and diluted with a small amount of propyl acetate and a little ether before storing in the refrigerator to promote crystallization. The product was filtered off and recrystallized from ethyl acetate/ether in the refrigerator to yield aldehyde coupler intermediate G ($R_1$=Et) (67 g, 89%).

Nitric acid (10.6 ml of 90% acid, density=1.57, 0.26 mole) was added dropwise over about 10 min to a solution of 4-t-octylphenol (50 g, 0.24 mole) in 500 ml of acetic acid kept at rt or below by means of an ice bath. The mixture was stirred for another 10 min after addition was complete and then diluted with 2.5 l of heptane. The heptane solution was washed 5 times with 1l portions of cold water and then once with 500 ml of brine. The heptane solution was then passed through about 2 l of silica gel in a large filter funnel. Additional lieptane containing 2 to 5% of ethyl acetate was used to elute the 2-nitro-4-t-octylphenol product as a yellow oil (49.8 g, 82%).

This oily phenol (182 g, 0.724 mole) was combined with 1.2 l of isopropyl alcohol and 12g of 5% Pd/C in a 5 flask fitted with uncooled condenser, mechanical stirrer, and 50° water bath. Ammonium formate (182 g, 2.9 mole) was added portionwise over about 15 min at such a rate as to avoid excessive foaming. Heating at 500 was continued for an additional 30 min before cooling to rt. Ethyl acetate (1.5 1) was added to dissolve the aminophenol before filtering the solution to remove catalyst. The filtrate was washed twice with salt water (700 ml water plus 300 ml brine) and then once with 300 ml of brine. After drying over $MgSO_4$ and concentrating to an oil, the product(2-amino-4-t-octylphenol, 154 g, 96%) crystallized was crystallized from 1.5 l of heptane.

A mixture of malononitrile (39.6 g, 0.6 mole), methanol (48 ml, 1.2 mole), and 180 ml of methyl formate was cooled to about 15°. Thionyl chloride (33.6 ml, 0.46 mole) was added dropwise to the vigorously stirred solution over about 45 min while keeping the temperature at 15–20°. The mixture was stirred for about 30 min more while a solid salt formed and then filtered. The solid was washed with methyl formate and then dried under a slow stream of nitrogen under vacuum to yield 57 g (69%) of hygroscopic solid methyl cyanoacetate-imino ester hydrochloride. This procedure was repeated a number of times and the combined product (194 g, 1.45 mole) was used immediately after drying by transferring to a 5-liter flask fitted with mechanical stirrer, heating mantle, and reflux condenser. Methanol (1.2 l) and 2-amino-4-t-octylphenol (160 g, 0.72 mole) were added before refluxing the mixture for 45 min. The mixture was cooled to rt and filtered. The filtrate was concentrated to a syrup, dissolved in 2 l of heptane, washed with 5'1l portions of water, washed once with 300 ml of brine, dried over $MgSO_4$, and concentrated again to syrupy cyanomethyl benzoxazole intermediate E (155 g, 80%).

A mixture of aldehyde coupler intermediate G ($R_1$=Et) (65 g, 0.117 mole), cyanomethyl benzoxazole intermediate E (34.9 g, 0.129 mole), DBU (1,8-diazabicyclo[5.4.0]undec-7-ene, 6 ml, 0.04 mole), and propyl acetate (250 ml) was stirred at rt for 2.3 hr. This mixture was washed with aqueous acid (25 ml of 2 N HCl plus 100 ml of water) and then with brine before drying over $MgSO_4$, filtering, and concentrating to a syrup. The syrup yielded crystalline nitro coupler intermediate H ($R_1$=Et) (84 g, 87%) from ether/heptane.

Nitro coupler intermediate H ($R_1$=Et) (5.08 g, 0.0063 mole) in 50 ml of toluene was reduced at 700 over 45 min by the addition of 700 mg of 5% Pd/C and 6.9 ml of 50% aqueous hypophosphorous acid. The mixture was filtered to remove catalyst, washed with 3:1 water:brine, dried over $MgSO_4$, and concentrated to gummy amino coupler intermediate I ($R_1$=Et) which crystallized from ether/heptane (4.3 g, 88%).

A suspension of 4-amino-1-naphthalene sulfonic acid (200 g, 0.897 mole) in 800 ml of pyridine was stirred mechanically while methanesulfonyl chloride (70 ml, 0.9 mole) was added slowly over about 10 min. The reaction warmed to about 600 as the solid dissolved and then slowly cooled to rt. The mixture was stirred overnight while a solid precipitated. After filtering and washing with 500 ml of ether, the solid was dried under a nitrogen stream to afford 211 g (62%) of 4-methanesulfonamido-1-naphthalene sulfonic acid pyridinium salt.

A suspension of the pyridinium salt (211 g, 0.555 mole), sodium sulfate (79 g, 0.555 mole), 1.1 l of acetonitrile, and phosphoryl chloride (201 ml, 2.2 mole) was stirred at rt for 16 hr. The reaction mixture was diluted with 2.5 l of ethyl acetate and washed 5 times with 1 l of ice water and then once with 500 ml of brine. The washed solution was dried over $MgSO_4$ and concentrated to a solid which was slurried in about a liter of heptane and filtered. The filter cake was dried under a stream of nitrogen to yield 158 g (89%) of 4-methafiesulfonamido-1-naphthalene sulfonyl chloride.

Amino coupler intermediate I ($R_1$=Et) (3.88 g, 0.005 mole) was dissolved in a mixture of 0.8 ml of pyridine, 5 ml of isopropanol, and 5 ml of tetrahydrofuran before adding 4-methanesulfonamido-1-naphthalene sulfonyl chloride (1.92 g, 0.006 mole) and stirring at rt for 30 min. The mixture was diluted with ethyl acetate and washed with 1N HCl and then brine. After drying over $MgSO_4$ and passing though a short pad of silica gel, the crude product was crystallized from ether/heptane to yield 4.3 g (81%) of coupler INV-5.

The following are the synthetic procedures for comparison Example 2. These are typical procedures for the synthesis of high dye yield yellow couplers when using the carbamyl chloride of the preformed methine dye (H).

A mixture of methyl-(4-methoxybenzoyl)acetate (97 g, 0.4 mole), 2-chloro-5-nitroaniline (72 g, 0.42 mole), and 500 ml of xylene was heated under reflux and a slow stream of nitrogen for 6 hr. The mixture was allowed to cool to rt and stirred overnight. The crystalline product which formed was filtered off, washed with ether, and dried to 124 g (85%) of coupler intermediate A.

Coupler intermediate A (34.9 g, 0.1 mole), 300 ml of dichloromethane, and 8.1 ml of sulfuryl chloride were mixed, stirred vigorously, and heated to reflux momentarily. The mixture was then stirred at room temperature for 2 hours while the solid dissolved as chlorination proceeded. The mixture was concentrated at reduced pressure to a solid which was slurried in ether, filtered, and dried to yield 36.6 g (95%) of chloro coupler intermediate B.

Triethylamine (40.5 ml) and formic acid (96%, 11 ml) were mixed with 90 ml of acetonitrile and cooled to room temperature. The mixture was stirred while chloro coupler intermediate B (36.6 g, 0.0955 mole) was added. After 1 hour the mixture was diluted with 120 ml of 1N HCl and stirred while a precipitate formed. The solid was filtered off, washed with water, and air dried to 36 g of crude product. After crystallization from methanol/tetrahydrofuran, 28.9 g (77%) of pure coupler intermediate C was obtained.

Coupler intermediate C (28.9 g, 0.073 mole) was dissolved in 120 ml of tetrahydrofuran. Methanol (120 ml) and 12 ml of conc. HCl were added before raising the temperature of the mixture momentarily to 40° with a warm water bath. The mixture was then stirred at room temperature and seeded with product crystals after 5 min. Water (15 ml) was added after 20 min and again after 1 hour (50 ml). The thick suspension was filtered after 1.25 hr, washed with water, a little 50% aqueous methanol, and then ether before drying to 22.5 g (84%) of hydroxy coupler intermediate D.

Nitric acid (10.6 ml of 90% acid, density=1.57, 0.26 mole) was added dropwise over about 10 min to a solution of 4-t-octylphenol (50 g, 0.24 mole) in 500 ml of acetic acid kept at room temperature or below by means of an ice bath. The mixture was stirred for another 10 min after addition was complete and then diluted with 2.5 l of heptane. The heptane solution was washed 5 times with 1-l portions of cold water and then once with 500 ml of brine. The heptane solution was then passed through about 2 l of silica gel in a large filter funnel. Additional heptane containing 2 to 5% of ethyl acetate was used to elute the 2-nitro-4-t-octylphenol product as a yellow oil (49.8 g, 82%).

This oily phenol (182 g, 0.724 mole) was combined with 1.2 l of isopropyl alcohol and 12g of 5% Pd/C in a 5 l flask fitted with uncooled condenser, mechanical stirrer, and 500 ml water bath. Ammonium formate (182 g, 2.9 mole) was added portionwise over about 15 min at such a rate as to avoid excessive foaming. Heating at 50° was continued for an additional 30 min before cooling to room temperature. Ethyl acetate (1.5 l) was added to dissolve the aminophenol before filtering the solution to remove catalyst. The filtrate was washed twice with salt water (700 ml water plus 300 ml brine) and then once with 300 ml of brine. After drying over $MgSO_4$ and concentrating to an oil, the product (2-amino-4-t-octylphenol, 154 g, 96%) was crystallized from 1.5 l of heptane.

A mixture of malononitrile (39.6 g, 0.6 mole), methanol (48 ml, 1.2 mole) and 180 ml of methyl formate was cooled to about 150. Thionyl chloride (33.6 ml, 0.46 mole) was added dropwise to the vigorously stirred solution over about 45 min while keeping the temperature at 15–20°. The mixture was stirred for about 30 min more while a solid salt formed and then filtered. The solid was washed with methyl formate and then dried under a slow stream of nitrogen under vacuum to yield 57 g (69%) of hygroscopic solid methyl cyanoacetate-imino ester hydrochloride. This procedure was repeated a number of times arid the combined product (194 g, 1.45 mole) was used immediately after drying by transferring to a 5-liter flask fitted with mechanical stirrer, heating mantle, and reflux condenser. Methanol (1.2 l) and 2-amino-4-t-octylphenol (160 g, 0.72 mole) were added before refluxing the mixture for 45 min. The mixture was cooled to room temperature and filtered. The filtrate was concentrated to a syrup dissolved in 2 l of heptane, washed with 5×1 l portions of water, washed once with 300 ml of brine, dried over $MgSO_4$, and concentrated again to syrupy cyanomethyl benzoxazole intermediate E (155 g, 80%).

Reduction of 4-nitroxylene with sodium sulfide to 4-amino-2-methylbenzaldehyde is reported in the literature [David A. Burgess and Ian D. Rae, *Aust. J. Chem.*, 1977, 30, 927–31; Lennart Florvall and Maj-Liz Persson, *Acta. Chemica. Scandinavica B*, 36 (1982) 141–146]. A homogeneous solution of sodium sulfide was prepared by mixing sodium sulfide nonahydrate (147 g, 0.615 mole), sodium hydroxide (53 g, 1.33 mole), elemental sulfur powder (27.8 g, 0.87 mole), and 950 ml of hot (55°) water in a 3 l flask equipped with mechanical stirrer, reflux condenser, and heating mantle. A solution of 4-nitrno-o-xylene (100.7 g, 0.67 mole) in 550 ml of ethanol was added before refluxing the mixture for 1.5 hr. The mixture of crude aldehyde was cooled to room temperature and treated with a solution of cyanomethyl benzoxazole intermediate E (150 g, 0.56 mole) in 190 ml of tetrahydrofuran plus 95 ml of ethanol. This mixture was stirred at room temperature for 2 hours while methine dye product precipitated. The dye was filtered off, washed with 500 ml of 50% aqueous methanol, washed with 500 ml of 80% methanol-water, and dried to yield 130 g (60%) of methine dye intermediate F.

Methine dye intermediate F (58.1 g, 0.15 mole) was dissolved in 150 ml of dimethylformamide and cooled to 0°. The solution was stirred while adding 16.8 ml of acetaldehyde followed by a solution of t-butylamino borane (t-BAB, 7.8 g, 0.09 mole) in 150 ml of acetic acid. Alkylated dye began to precipitate after a few minutes so the mixture was warmed to room temperature, stirred for 30 min, and then diluted with 100 ml of 50% aqueous methanol. The dye was; filtered off, washed with methanol, dissolved in dichloromethane, concentrated, and re-precipitated with methanol to yield pure methine dye intermediate G (46.6 g, 75%).

Methine dye intermediate G (46.6 g, 0.112 mole) was dissolved in a solution of 2,6-lutidine (14 ml, 0.12 mole) and 300 ml of dichloromethane. The mixture was stirred vigorously at room temperature while adding phosgene (60 ml of 2M solution in toluene, 0.12 mole). After 30 min the solution was washed with 1N HCl, dried over $MgSO_4$, and passed though a small pad of silica gel to remove polar impurities using 10% ether in dichloromethane to elute the product dye carbamyl chloride intermediate H (crystallized from heptane, 49.6 g, 93%).

Hydroxy coupler intermediate D (8 g, 0.022 mole), methine dye carbamyl chloride intermediate H (10.5 g, 0.022 mole), dimethylaminopyridine (3.2 g, 0.0264 mole), 3A molecular sieves (22 g), and 60 ml of dichloroethane were stirred under nitrogen atmosphere for 30 min. After washing the mixture with 1N HCl and concentrating to a syrup, the crude product was chromatographed on 400 g of silica gel using 2–10% acetonitrile in toluene as eluent. Nitro coupler intermediate I (6 g, 31%) was obtained as a crystalline solid from ether/heptane.

Nitro coupler intermediate I (5.08 g, 0.0063 mole) in 50 ml of toluene was reduced at 70° over 45 min by the addition of 700 mg of 5% Pd/C and 6.9 ml of 50% aqueous hypophosphorous acid. The mixture was filtered t) remove catalyst, washed with 3:1 water:brine, dried over $MgSO_4$, and concentrated to gummy amino coupler intermediate J which crystallized from ether/heptane (4.3 g, 88%).

A suspension of 4-amino-1-naphthalene sulfonic acid (200 g, 0.897 mole) in 800 ml of pyridine was stirred mechanically while methanesulfonyl chloride (70 ml, 0.9 mole) was added slowly over about 10 min. The reaction warmed to about 60° as the solid dissolved and then slowly cooled to room temperature. The mixture was stirred overnight while a solid precipitated. After filtering and washing with 500 ml of ether, the solid was dried under a nitrogen stream to afford 211 g (62%) of 4-methanesulfonamido-1-naphthalene sulfonic acid pyridinium salt.

A suspension of the pyridinium salt (211 g, 0.555 mole), sodium sulfate (79 g, 0.555 mole), 1.1 l of acetonitrile, and phosphoryl chloride (201 ml, 2.2 mole) was stirred at room temperature for 16 hours. The reaction mixture was diluted with 2.5 l of ethyl acetate and washed 5 times with 1 l of i,e water and then once with 500 ml of brine. The washed solution was dried over $MgSO_4$ and concentrated to a solid which was slurried in about a liter of heptane and filtered. The filter cake was dried under a stream of nitrogen to yield 158 g (89%) of 4-methanesulfonamido-1-naphthalene sulfonyl chloride.

Amino coupler intermediate J (3.88 g, 0.005 mole) was dissolved in a mixture of 0.8 ml of pyridine, 5 ml of isopropanol, and 5 ml of tetrahydrofuran before adding 4-methanesulfonamido-1-naphthalene sulfonyl chloride (1.92 g, 0.006 mole) and stirring at rt for 30 min. The mixture was diluted with ethyl acetate and washed with 1N HCl and then brine. After drying over $MgSO_4$ and passing though a short pad of silica gel, the crude product was crystallized from ether/heptane to yield 4.3 g (81%) of solubilized coupler Inv-5.

The following schemes show two more examples of high dye-yield yellow couplers, Inv-1 and Inv-42. The examples illustrate the method of making the carbamyl chlorides of aminoarylcarbonyl compounds and the method of using them in the preparation of high dye-yield yellow couplers, as the current invention states. Example 3 illustrates the synthesis of a high-dye yield yellow coupler with a timing group, Inv-1. Example 4 illustrates the synthesis of a high dye-yield yellow coupler without a timing group, Inv-42.

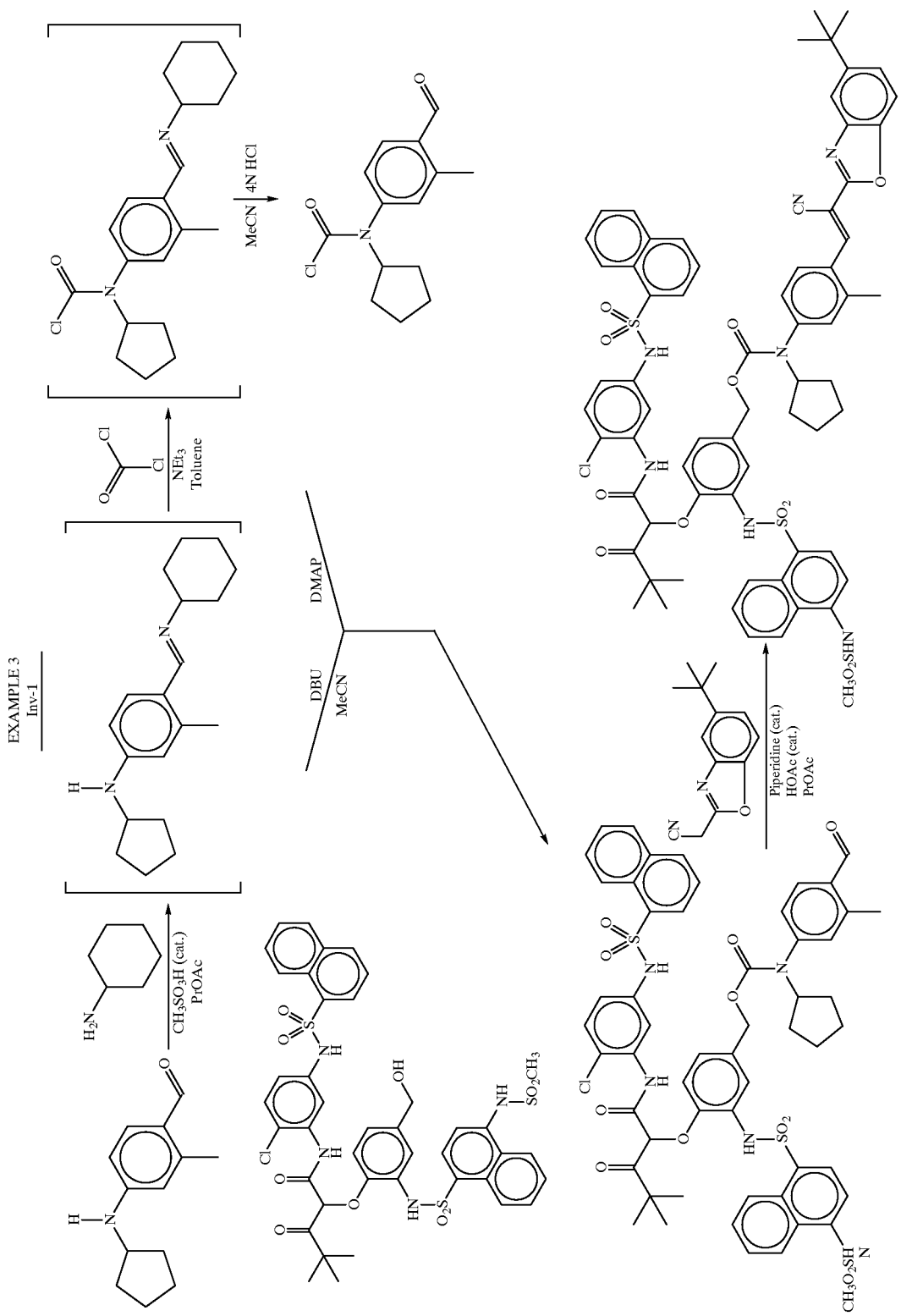

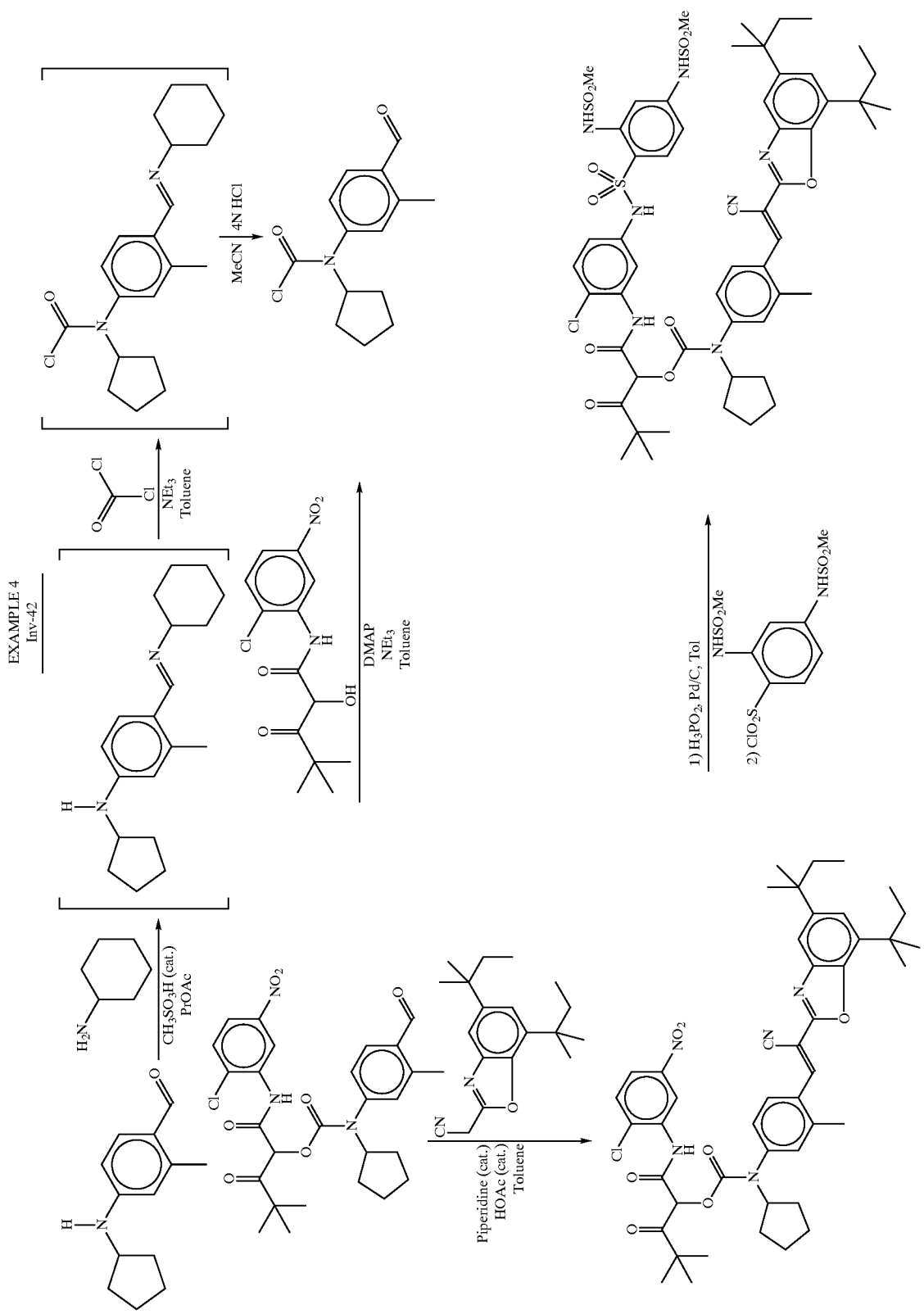

Synthetic Procedures for Example 3

In a 1-l flask, place 40.66 g (0.2 m) of 4-cyclopentylamino-2-methylbenzaldehyde, 300 ml of propyl acetate, and 20.83 g (0.21 m) of cyclohexylamine. Stir the mixture to a solution. Add 1.0 g of methanesulfonic acid. Heat the mixture under reflux collecting water formed during the reaction. With a vigorous reflux, theoretical amount of water (3.6 ml) is collected in a Dean-Stark trap within an hour. Keep refluxing for additional 30 minutes and then distill off about 50 ml of propyl acetate at the end of refluxing time to make sure that Schiff base formation is complete. Cool the mixture to room temperature and then 0–5 C in an ice bath. Add 35.4 g (0.35 m) of triethylamine and 160 ml (0.3 m) of 20% phosgene in toluene (d 0.935) from a dropping funnel over 20 min keeping the temperature at or below 20 C. Stir the mixture at room temperature for 1.5 hours. Degas and distill solvents under a reduced pressure keeping the pot temperature at 30–35 C till no distillate comes off and a viscous oil left in the flask. Add 350 ml of acetonitrile and stir to dissolve the oil. Add 200 ml of 4N HCl and stir the mixture at room temperature for 2 hours. Add 200 ml of isopropyl ether and 200 ml of water (or more to fill-up to capacity of flask). Separate bottom water layer and wash upper organic layer with 250 ml of 1N HCl twice. Dry over magnesium sulfate and distill off solvent under a reduced pressure to give 48.1 g (90.5%) of light brown oil. This oil can be used as it is in the next step. To isolate pure carbamyl chloride, dissolve the oil in 100 ml of isopropyl ether and evaporate the solvent with no heat till product crystallizes and the mixture becomes a thick slurry. Let the mixture stand at 0–5 C in an ice bath for at least 2–3 hours to get maximum return. Collect product with help of 1:1 (v/v) isopropyl ether-heptanes, wash with same mixed solvents, and dry to give 39.4 g (74%) of carbamyl chloride of 4-cyclopentylamino-2-methylbenzaldehyde.

In a 1-l flask inserted with nitrogen, place 43.97 g (0.05 m) of coupler-timing group piece shown in the scheme of Example 3 and 200 ml of acetonitrile. Stir the mixture to a suspension with nitrogen bubbling. Add 33.5 g (0.22 m) of DBU as a steady stream. Exotherm to 30–35 C and clear solution occurs. Cool the solution to room temperature.

Add 6.72 g (0.055 m) of DMAP and 14.62 g (0.055 m) of carbamyl chloride of 4-cyclo-pentylamino-2-methylbenzaldehyde in 6 equal portions in 5 hours with 1 hour interval between each addition. After the final addition, keep stirring the mixture at room temperature for additional 3 hours. Add 300 ml of 4N HCl and 350 ml of propyl acetate. Stir for a few minutes and let layers settle. Separate bottom water layer. Concentrate upper propyl acetate solution under a reduced pressure at a pot temperature of 50–60 C to a thick oil or a solid gum. Remove the heat source. Add 270 ml of propyl acetate to the mixture with a good stirring and add approximately 4 g of Celite. Filter insolubles through a Celite pad and wash with 30 ml of propyl acetate. Add 40 g of silica gel to the filtrate and stir for 5 min. Filter off the silica gel and wash with 50 ml of propyl acetate. The filtrate contains a reasonably pure coupler-timing group-aminoarylcarbonyl intermediate and can be used as it is in the next step.

Place the filtrate in the original 1-l flask. Add 10. 71 g (0.05 m) of 5-t-butyl-2-cyanomethylbenzoxazole, 0.3 g of piperidine and 0.9 g of acetic acid. Stir the mixture at 60–65 C for 1 hour and slowly distill under a reduced pressure at 50–55 C pot temperature (60–65 C bath temperature) collecting initially an water/propyl acetate azeotrope and the propyl acetate till approximately 1 ml of water and 150 ml of propyl acetate is collected over 2 hour period. Run a TLC to confirm the reaction complete. Add 100 ml of water, stir for a minutes and layers settle. Separate water layer off. Distill about 50 ml of propyl acetate under a reduced pressure at 50–55 C pot temperature. Add 75 ml of isopropyl ether with a good stirring. Cool to room temperature and then to 0–3 C in an ice bath. Add seeds and stir at 0–3 C for 3 hours. Let the mixture stand at 0–3 C in an ice bath overnight. Collect product, wash with 2:1 (v/v) mixture of propyl acetate-isopropyl ether till washings are colorless, and dry to give 45.7 g (70%) of the coupler of Example 3 as bright yellow solids.

Synthetic Procedures for Example 4

The carbamyl chloride 4-cyclopentylamino-2-methylbenzaldehyde is made in the same way as in the Synthesis of Example 3 above.

In a 1-l flask inerted with nitrogen, place 26.57 g (0.1 m) of the carbamyl chloride, 12.22 g (0.1 m) of DMAP, and 350 ml of toluene. Stir the mixture at room temperature for 5 minutes. Add 31.47 g (0.1 m) of N-2-chioro-5-nitrophenyl-4,4-dimethyl-2-hydroxy-1,3-dioxopentanamide and 12.14 g (0.12 m) of triethylamine. Stir the mixture at 30 C for 2 hours. Run a TLC to confirm the reaction complete. Add 300 ml of 2N HCl with vigorous stirring. Filter insolubles through a Celite pad and wash with 100 ml of toluene. Separate bottom water layer. Wash toluene solution twice with 300 ml of 2N HCl each and dry over magnesium sulfate. The toluene solution contains a reasonably pure coupler-aminoarylcarbonyl compound and can be used as it is in the next step. The yield for this step was 84%.

Place the toluene solution in the original 1-l flask and 29.84 g (0.1 m) of 2-cyanomethyl-5,7-di-t-pentylbenzoxazole. Add 0.6 g of piperidine and 1.8 g of acetic acid. Stir the mixture at 60–65 C for 1 hour and slowly distill under a reduced pressure at 60–65 C pot temperature (70–75 C bath temperature) collecting initially an azeotrope of water- toluene and the toluene till approximately 1.8 ml of water and 150 ml of toluene is collected over 2 hour period. Run a TLC to confirm the reaction complete. Cool the reaction mixture to room temperature. Add 300 ml of 1N HCL, stir for a few minutes and layers settle. Separate water layer and distill toluene under a reduced pressure at 60–65 C pot temperature till no distillate comes off. Add 250 ml of methanol and heat to boil to dissolve viscous. Cool the methanol solution to room temperature with stirring. Continue to stir the resulting slurry at 15 C for 2 hours. Collect solid, wash with methanol, and dry to give 60.2 g (73%) of nitro coupler intermediate as yellow solids.

In a 1-l flask, place 65.95 g (0.08 m) of the above nitro compound, 250 ml of toluene, and 80 ml of water. Add 5.28 g of 5% Pd/C 50% wet. and 20 ml of water. Add 63.36 g (0.48 m) of 50% hypophosphorous acid. Stir the mixture in maximum speed at 70–75 C for 3 hours. Filter through a Celite pad to collect catalyst and wash with 50 ml of toluene and 25 ml of water. Cool the filtrate to room temperature. Add a solution of 19.2 g (0.48 m) of NaOH in 100 ml of water with a gentle stirring. Let layers settle and separate bottom water layer. Concentrate toluene solution by distillation under a reduced pressure till no distillate comes off. Add 250 ml of propyl acetate and 125 ml of acetonitrile, and stir to dissolve gummy intermediate. Add 1.52 g of pyridine N-oxide and stir for 10 minutes. Add 40.64 g (0.112 m) of 2,4-dimethylsulfonylaminnobenzenesulfonyl chloride and stir for 5 minutes. Add 17.72 g (0.224 m) of pyridine dropwise from a dropping funnel at room temperature over a period of 60–75 minutes. Stir the mixture at room temperature for another 30 minutes. Add 250 ml of water and stir for 30 minutes. Let it stand for 15 minutes for layers to be settled, and separate water layer. Add 250 ml of d-HCl (12.5 ml of c-HCL diluted to 250 ml), stir for a few minutes, let layers settle for 15 minutes, and separate water layer. Drop propyl acetate solution by azeotropic distillation under a reduced pressure at a pot temperature of 50–55 C, collecting 50–100 ml of distillate depending on amount of water. Cool propyl acetate solution to room temperature and filter through a 10 g of silica gel bed and wash with 100 ml of propyl acetate. Concentrate propyl acetate solution by distillation under a reduced pressure at a pot temperature of 55–60 C till no distillate comes off. Add 500 ml of preheated methanol and stir to dissolve viscous product oil. As soon as the solution occurs, stop stirring, remove heat source, and let it cool to room temperature by itself and stand at room temperature for at least 4–5 hours. Collect solids, wash with 100 ml of methanol portionwise, pack down soft solids under a rubber dam and wash again with another 100 ml of methanol portionwise and 50 ml of heptanes. Dry the solids in a vacuum oven to give 82.5 g (92%) of the coupler of Example 4 as yellow fluffy sclids.

The invention has been described above with particular reference to preferred embodiments thereof. A skilled worker being aware of the above detailed description can make many modifications or substitutions without departing from the scope or spirit of this invention. The entire contents of the patents and other publications referred to in this specification are incorporated herein by reference.

What is claimed is:

1. A carbamyl chloride of an aminoarylcarbonyl compound having the structural formula I:

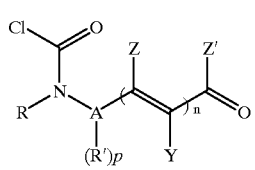

Formula I wherein
R is an alkyl, alkenyl, or aryl group;
A is an aryl group;
each R' is independently an alkyl group which may form a ring with Z or Z';
p is 0, 1, 2, or 3;
each Z and Z', is independently hydrogen or an alkyl group that may form a ring with R';
Y is hydrogen or an alkyl group; and
n is 0, 1, or 2.

2. The compound of claim 1 wherein R is an alkyl or alkenyl group having 1–22 carbon atoms.

3. The compound of claim 1 wherein R is a hindered alkyl group having at least 3 carbon atoms.

4. The compound of claim 3 wherein R is an isopropyl, sec-butyl, 2-pentyl, 2-hexyl, cyclopropyl, cyclobutyl, cyclopentyl, cyclohexyl, 1-phenylethyl, 1-phenylpropyl, or 1-phenylbutyl group.

5. The compound of claim 3 wherein R is a cyclopentyl group.

6. The compound of claim 1 wherein one or more R' is an alkyl group having 1 to 5 carbon atoms.

7. The compound of claim 6 wherein one or more R' is a methyl, ethyl, propyl, isopropyl, butyl, sec-butyl, t-butyl, pentyl, or neopentyl group.

8. The compound of claim 7 wherein one R' is a methyl group.

9. The compound of claim 1 wherein A is a phenyl or naphthyl group.

10. The compound of claim 9 wherein A is a phenyl group.

11. The compound of claim 10 wherein Z' is H.

12. The compound of claim 1 wherein Z' is H.

13. A method of making a carbamyl chloride of Formula I of claim 1, comprising the steps of:
 (a) blocking the carbonyl function of an aminoarylcarbonyl compound via Schiff base formation with a hindered alkyl amine;
 (b) making a carbamyl chloride of the blocked aminoarylcarbonyl compound by phosgenation; and
 (c) deblocking the carbamyl chloride of the blocked aminoarylcarbonyl via acid hydrolysis to regenerate the carbonyl function and give the desired carbamyl chloride of an aminoarylcarbonyl compound having formula I wherein R, A, R', p, Z, Y, n, and Z' are as defined in claim 1.

14. The method of claim 13 wherein blocking step (a) is done via Schiff base formation with an alkyl amine branched at the alpha carbon.

15. The method of claim 14 wherein the amine is t-butylarnine, cyclohexylamine, or t-octylamine.

16. The method of claim 15 wherein the amine is cyclohexylamine.

* * * * *